United States Patent
Lechner et al.

(10) Patent No.: US 11,439,578 B2
(45) Date of Patent: Sep. 13, 2022

(54) AGENT FOR DYEING HAIR, CONTAINING AT LEAST ONE ORGANIC SILICON COMPOUND, A COLORING COMPOUND AND A FILM-FORMING, HYDROPHILIC POLYMER

(71) Applicant: Henkel AG & Co. KGaA, Duesseldorf (DE)

(72) Inventors: Torsten Lechner, Langenfeld (DE); Marc Nowottny, Moenchengladbach (DE); Juergen Schoepgens, Schwalmtal (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 88 days.

(21) Appl. No.: 17/052,085

(22) PCT Filed: Mar. 21, 2019

(86) PCT No.: PCT/EP2019/057027
§ 371 (c)(1),
(2) Date: Oct. 30, 2020

(87) PCT Pub. No.: WO2019/214871
PCT Pub. Date: Nov. 14, 2019

(65) Prior Publication Data
US 2021/0361551 A1    Nov. 25, 2021

(30) Foreign Application Priority Data

Mar. 7, 2018   (DE) .................... 10 2018 207 025.3

(51) Int. Cl.
| | |
|---|---|
| *A61Q 5/10* | (2006.01) |
| *A61K 8/58* | (2006.01) |
| *A61K 8/26* | (2006.01) |
| *A61K 8/34* | (2006.01) |
| *A61K 8/365* | (2006.01) |
| *A61K 8/37* | (2006.01) |
| *A61K 8/39* | (2006.01) |
| *A61K 8/44* | (2006.01) |
| *A61K 8/81* | (2006.01) |
| *A61Q 5/12* | (2006.01) |

(52) U.S. Cl.
CPC .............. *A61K 8/585* (2013.01); *A61K 8/26* (2013.01); *A61K 8/342* (2013.01); *A61K 8/345* (2013.01); *A61K 8/365* (2013.01); *A61K 8/375* (2013.01); *A61K 8/39* (2013.01); *A61K 8/442* (2013.01); *A61K 8/8164* (2013.01); *A61K 8/8176* (2013.01); *A61Q 5/10* (2013.01); *A61Q 5/12* (2013.01); *A61K 2800/4324* (2013.01); *A61K 2800/87* (2013.01); *A61K 2800/884* (2013.01)

(58) Field of Classification Search
CPC . A61Q 5/10; A61Q 5/065; A61Q 5/12; A61K 2800/88; A61K 2800/884; A61K 2800/87; A61K 8/25; A61K 8/585; A61K 8/8182; A61K 2800/432; A61K 8/8176; A61K 8/8164
USPC .......................................................... 8/405
See application file for complete search history.

(56) References Cited

U.S. PATENT DOCUMENTS

| | | | |
|---|---|---|---|
| 6,746,492 B2 | 6/2004 | Kawai et al. | |
| 7,806,941 B2 | 10/2010 | Brun et al. | |
| 2010/0083446 A1* | 4/2010 | Brun | A61K 8/891 |
| | | | 8/405 |

FOREIGN PATENT DOCUMENTS

| | | |
|---|---|---|
| DE | 10200185 A1 | 7/2002 |
| EP | 1532967 A1 | 5/2005 |
| EP | 2168633 A2 | 3/2010 |

OTHER PUBLICATIONS

STIC Search Report dated Jan. 12, 2022.*
EPO, International Search Report issued in International Application No. PCT/EP2019/057027, dated May 17, 2019.

* cited by examiner

*Primary Examiner* — Eisa B Elhilo
(74) *Attorney, Agent, or Firm* — Lorenz & Kopf, LLP

(57) ABSTRACT

The subject of the present disclosure is a composition for coloring keratinous material, in particular human hair, containing in a cosmetic carrier
(a) at least one organic silicon compound selected from silanes having one, two or three silicon atoms, said organic silicon compound further comprising one or more basic chemical functions and one or more hydroxyl groups or hydrolysable groups per molecule,
(b) at least one colorant compound from the group of pigments and/or direct dyes, and
(c) at least one film-forming hydrophilic polymer.

20 Claims, No Drawings

AGENT FOR DYEING HAIR, CONTAINING AT LEAST ONE ORGANIC SILICON COMPOUND, A COLORING COMPOUND AND A FILM-FORMING, HYDROPHILIC POLYMER

CROSS-REFERENCE TO RELATED APPLICATION

This application is a U.S. National-Stage entry under 35 U.S.C. § 371 based on International Application No. PCT/EP2019/057027, filed Mar. 21, 2019, which was published under PCT Article 21(2) and which claims priority to German Application No. 10 2018 207 025.3, filed May 7, 2018, which are all hereby incorporated in their entirety by reference.

TECHNICAL FIELD

The subject-matter of the present application is a composition for coloring keratinous material, in particular human hair, comprising, in a cosmetic carrier, (a) at least one specific organic silicon compound, (b) at least one coloring compound chosen from the group including pigments and/or direct dyes and (c) at least one film-forming hydrophilic polymer.

Another subject of this notification is a kit-of-parts for dyeing keratinous material, in particular human hair, which comprises the agents (I), (II) and (III) separately packaged in three different containers. Here, agent (I) contains at least one organic silicon compound (a), agent (II) contains water, and agent (III) contains at least one direct-acting dye (b) and at least one film-forming, hydrophilic polymer (c).

A third object of the present disclosure is a process for dyeing keratinous material, which comprises the application of a pretreatment agent (V) and subsequently the application of a colorant (F). Here, the pretreatment agent (V) contains at least one special organic silicon compound (a) in a water-containing cosmetic carrier.

The colorant (F) is exemplified by its content of at least one direct dye (b) and at least one film-forming, hydrophilic polymer (c).

BACKGROUND

The change in shape and color of keratin fibers, especially hair, is an important area of modern cosmetics. To change the hair color, the expert knows various coloring systems depending on coloring requirements. Oxidation dyes are usually used for permanent, intensive dyeings with good fastness properties and good grey coverage. Such dyes usually contain oxidation dye precursors, so-called developer components and coupler components, which form the actual dyes with one another under the influence of oxidizing agents, such as hydrogen peroxide. Oxidation dyes are exemplified by very long-lasting dyeing results.

When direct dyes are used, ready-made dyes diffuse from the colorant into the hair fiber. Compared to oxidative hair dyeing, the dyeing obtained with direct dyes have a shorter shelf life and quicker washability. Dyeing with direct dyes usually remains on the hair for a period of between about 5 and about 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents containing surfactants. Various products of this type are available on the market under the name hair mascara.

If the user wants particularly long-lasting dyeings, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair.

EP 2168633 B1 deals with the task of producing long-lasting hair colorations using pigments. It teaches that by using a combination of pigment, organic silicon compound, hydrophobic polymer, and a solvent, it is possible to create colorations on hair that are particularly resistant to shampooing.

During the revision of the doctrine of EP 2168633 B1, its formulations have been adjusted. It has been shown that one disadvantage of these formulations is their poor storage stability. With the pigments and the hydrophobic polymers, the formulations contain very poorly soluble substances that, although they could be brought into dispersion for a short time when the formulations were manufactured, conglomerated, settled or separated from the water phase over longer storage periods. Depending on the chosen application concentration of pigment and hydrophobic polymer, it has also proved difficult to get the poorly soluble substances sufficiently finely dispersed in a dispersion directly during production.

BRIEF SUMMARY

The purpose of the present disclosure was to provide a dyeing system with fastness properties comparable to those of oxidative dyeing. Wash fastness properties should be outstanding, but the use of oxidation dye precursors normally used for this purpose should be avoided. A technology was sought that would make it possible to fix the coloring compounds known from state-of-the-art technology (such as pigments and direct dyes) to the hair in an extremely permanent manner. A sufficiently high storage stability of the formulations should be guaranteed. In addition, the production process of the formulations should also be simplified or optimized.

Surprisingly, it has now turned out that the above-mentioned task can be excellently solved if keratinous materials, in particular human hair, are dyed with a composition containing, in a cosmetic carrier, at least one specific organic silicon compound, at least one colorant compound from the group of pigments and/or direct dyes and at least one film-forming hydrophilic polymer.

Cosmetic compositions, methods for using cosmetic compositions, and kits of parts of cosmetic compositions are provided. In an exemplary embodiment, a composition for dyeing keratinous material includes (a) an organic silicon compound selected from silanes with 1, 2, or 3 silicon atoms, one or more basic chemical functions, and one or more hydroxyl groups or hydrolysable groups per molecule. The composition further includes (b) at least one colorant compound selected from the group of pigments, direct dyes, and combinations thereof, and (c) at least one film-forming hydrophilic polymer.

A kit of parts for dyeing keratinous material is provided in another embodiment. The kit of parts includes a first container with a cosmetic product (I), a second container with a cosmetic product (II), and a third container with a cosmetic product (III). The cosmetic product (I) includes an organic silicon compound (a) selected from silanes having 1, 2, or 3 silicon atoms, one or more basic chemical functions, and one or more hydroxyl groups or hydrolysable groups per molecule. The cosmetic product (II) includes water, and the cosmetic product (III) includes a colorant compound (b) selected from the group of pigments, direct dyes, and combinations thereof, and a film-forming polymer (c).

A method of dyeing keratinous materials is provided in yet another embodiment. The method includes applying a pretreatment agent (V) to the keratinous material, where the pretreatment agent (V) includes, in a water-containing cosmetic carrier, an organic silicon compound (a) selected from silanes having 1, 2, or 3 silicon atoms, a basic chemical function, and a hydroxyl group or a hydrolysable group per molecule. A coloring agent (F) is applied to the keratinous material, where the coloring agent (F) includes a colorant compound (b) selected from pigments, direct dyes, and combinations thereof, and a film-forming polymer (c).

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

A first object of the present disclosure is therefore an agent for coloring keratinous material, in particular human hair, containing in a cosmetic carrier
(a) at least one organic silicon compound selected from silanes having one, two or three silicon atoms, said organic silicon compound further comprising one or more basic chemical functions and one or more hydroxyl groups or hydrolysable groups per molecule,
(b) at least one colorant compound from the group of pigments and/or direct dyes, and
(c) at least one film-forming hydrophilic polymer.

In the course of the work leading to this disclosure, it was found that the incorporation of the present disclosure's organic silicon compounds (a), coloring compounds (b) and film-forming hydrophilic polymers (c) into a cosmetic carrier resulted in formulations with excellent storage stability. Without being limited to this theory, it is assumed in this context that the highly soluble, film-forming polymers (c) keep the coloring compounds in dispersion or prevent their settling or separation. The production of the formulations was also simplified, since the hydrophilic polymers were quite easy to bring into solution due to their good water solubility. It proved to be particularly advantageous that particularly stable formulations could be produced in this way even without the use of large quantities of surfactants.

Surprisingly, it was also found that despite the use of a hydrophilic, i.e. actually highly water-soluble polymer (c) together with the other ingredients (a) and (b), a very resistant film could be produced on the keratinic material. For this reason, the keratinic material has been given extremely fast colors with good resistance to shampooing.
Agent for Dyeing Keratinous Material Keratinous material includes hair, skin, and nails (such as fingernails and/or toenails). Wool, furs, and feathers also fall under the definition of keratinous material.

Preferably, keratinous material is understood to be human hair, human skin, and human nails, especially fingernails and toenails. Keratinous material is understood to be human hair.

The compositions as contemplated herein contain the compounds (a), (b) and (c) essential to the present disclosure in a cosmetic carrier, preferably in a suitable aqueous or aqueous-alcoholic carrier. For hair coloration, such carriers are, for example, creams, emulsions, gels, or surfactant-containing foaming solutions, such as shampoos, foam aerosols, foam formulations or other preparations suitable for application to the hair.

The cosmetic carrier preferably contains water, which means that the carrier contains at least about 2% by weight of water based on its weight. Preferably, the water content is above about 5 wt. %, further preferably above about 10 wt. %, still further preferably above about 15 wt. %. The cosmetic carrier can also be aqueous alcoholic. Aqueous/alcoholic solutions in the context of the present disclosure are aqueous solutions containing from about 2 to about 70% by weight of a $C_1$-$C_4$ alcohol, more particularly ethanol or isopropanol. The agents as contemplated herein may additionally contain other organic solvents, such as methoxy butanol, benzyl alcohol, ethyl diglycol or 1,2-propylene glycol. Preferred are all water-soluble organic solvents.

The term "dyeing agent" is used in the context of this disclosure for a coloration of the keratin material, of the hair, caused using pigments and/or direct dyes. In this staining process, the colorant compounds are deposited in a particularly homogeneous and smooth film on the surface of the keratin material or diffuse into the keratin fiber. The film is formed in situ by oligomerization or polymerization of the organic silicon compound(s), and by the interaction of the coloring compound and organic silicon compound with the film-forming hydrophilic polymer.

Organic Silicon Compounds

As a first-essential ingredient (a) of the present disclosure, the compositions of the present disclosure contain at least one organic silicon compound selected from silanes having one, two or three silicon atoms, said organic silicon compound further comprising one or more basic chemical functions and one or more hydroxyl groups or hydrolysable groups per molecule.

Organic silicon compounds, alternatively called organosilicon compounds, are compounds which either have a direct silicon-carbon bond (Si—C) or in which the carbon is bonded to the silicon atom via an oxygen, nitrogen, or sulfur atom. The organic silicon compounds as contemplated herein are compounds containing one to three silicon atoms. Organic silicon compounds preferably contain one or two silicon atoms.

The organic silicon compounds (a) contain at least one basic group. This basic group can be, for example, an amino group, an alkylamino group or a dialkylamino group, which is preferably connected to a silicon atom via a linker.

Furthermore, the organic silicon compounds include at least one hydroxy group or a hydrolysable group. The hydrolysable group(s) is (are) preferably a $C_1$-$C_6$ alkoxy group, especially an ethoxy group or a methoxy group. It is preferred when the hydrolysable group is directly bonded to the silicon atom. For example, if the hydrolysable group is an ethoxy group, the organic silicon compound preferably contains a structural unit R'R"R'"Si—O—CH2-CH3. The residues R', R' and R'" represent the three remaining free valences of the silicon atom.

Particularly good results could be obtained if the compositions as contemplated herein contained at least one organic silicon compound (a) of formula (I) and/or (II), In another preferred embodiment, an agent as contemplated herein contains at least one organic silicon compound (a) of formula (I) and/or (II).

where
R$_1$, R$_2$ independently represent a hydrogen atom or a C$_1$-C$_6$ alkyl group,
L is a linear or branched divalent C$_1$-C$_{20}$ alkylene group,
R3 represents a hydrogen atom or a C$_1$-C$_6$ alkyl group
R4 represents a C$_1$-C$_6$ alkyl group
a, stands for an integer from 1 to 3, and
b stands for the integer 3-a,

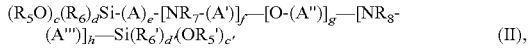

where
R5, R5', R5" independently represent a hydrogen atom or a C$_1$-C$_6$ alkyl group,
R6, R6' and R6" independently represent a C$_1$-C$_6$ alkyl group,
A, A', A", A''', and A"" independently of one another represent a linear or branched divalent C$_1$-C$_{20}$ alkylene group
R$_7$ and R$_8$ independently represent a hydrogen atom, a C$_1$-C$_6$ alkyl group, a hydroxy C$_1$-C$_6$ alkyl group, a C$_2$-C$_6$ alkenyl group, an amino C$_1$-C$_6$ alkyl group or a group of formula (III)

c, stands for an integer from 1 to 3,
d stands for the integer 3-c,
c' stands for an integer from 1 to 3,
d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
provided that at least one of e, f, g, and h is different from 0.

The substituents R$_1$, R$_2$, R$_3$, R$_4$, R$_5$, R$_5$', R$_5$", R$_6$, R$_6$', R$_6$", R$_7$, R$_8$, L, A, A', A", A''' and A""—" in the compounds of formula (I) and (II) are explained below as examples:

Examples of a C$_1$-C$_6$ alkyl group are the groups methyl, ethyl, propyl, isopropyl, n-butyl, s-butyl, and t-butyl, n-pentyl and n-hexyl. Propyl, ethyl, and methyl are preferred alkyl radicals. Examples of a C$_2$-C$_6$ alkenyl group are vinyl, allyl, but-2-enyl, but-3-enyl and isobutenyl, preferred C$_2$-C$_6$ alkenyl radicals are vinyl and allyl. Preferred examples of a hydroxy C$_1$-C$_6$ alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino C$_1$-C$_6$ alkyl group are the aminomethyl group, the 2-aminoethyl group, the 3-aminopropyl group. The 2-aminoethyl group is particularly preferred. Examples of a linear divalent C$_1$-C$_{20}$ alkylene group include the methylene group (—CH$_2$—,), the ethylene group (—CH$_2$—CH$_2$—), the propylene group (—CH$_2$—CH$_2$—CH$_2$—) and the butylene group (—CH$_2$—CH$_2$—CH$_2$—CH$_2$—). The propylene group (—CH$_2$—CH$_2$—CH$_2$—) is particularly preferred. From a chain length of 3 C atoms, divalent alkylene groups can also be branched. Examples of branched divalent C$_3$-C$_{20}$ alkylene groups are (—CH$_2$—CH(CH$_3$)—) and (—CH$_2$—CH(CH$_3$)—CH$_2$—).

In the organic silicon compounds of the formula (I)

the radicals R$_1$ and R$_2$ independently of one another represent a hydrogen atom or a C$_1$-C$_6$ alkyl group. In particular, the radicals R$_1$ and R$_2$ both represent a hydrogen atom.

In the middle part of the organic silicon compound is the structural unit or the linker -L- which stands for a linear or branched, divalent C$_1$-C$_{20}$ alkylene group.

Preferably -L- stands for a linear, divalent C$_1$-C$_{20}$ alkylene group. Further preferably -L- stands for a linear divalent C$_1$-C$_6$ alkylene group. Particularly preferred -L- stands for a methylene group (CH$_2$—), an ethylene group (—CH$_2$—CH$_2$—), propylene group (—CH$_2$—CH$_2$—CH$_2$—) or butylene (—CH$_2$—CH$_2$—CH$_2$—CH$_2$—). L stands for a propylene group (—CH$_2$—CH$_2$—CH$_2$—)

In another preferred embodiment, an agent as contemplated herein contains (a) at least one organic silicon compound of formula (I), R$_1$R$_2$N-L-Si(OR$_3$)$_a$(R$_4$)$_b$       (I), where
R$_1$, R$_2$ both represent a hydrogen atom, and
L represents a linear, divalent C$_1$-C$_6$-alkylene group, preferably a propylene group (—CH$_2$—CH$_2$—CH$_2$—) or an ethylene group (—CH$_2$—CH$_2$—).

The organic silicon compounds of formula (I)

R$_1$R$_2$N-L-Si(OR$_3$)$_a$(R$_4$)$_b$       (I), carry the silicon-containing group —Si(OR$_3$)$_a$(R$_4$)$_b$ at one end.

In the terminal structural unit —Si(OR$_3$)$_a$(R$_4$)$_b$, R$_3$ is hydrogen or C$_1$-C$_6$ alkyl group, and R$_4$ is C$_1$-C$_6$ alkyl group. R$_3$ and R$_4$ independently of each other represent a methyl group or an ethyl group.

Here a stands for an integer from 1 to 3, and b stands for the integer 3-a. If a stands for the number 3, then b is equal to 0. If a stands for the number 2, then b is equal to 1. If a stands for the number 1, then b is equal to 2.

Dyes with the best wash fastness values could be obtained if the pretreatment agent contains at least one organic silicon compound corresponding to formula (I): in which R$_3$, and R$_4$ independently of one another represent a methyl group or an ethyl group.

Furthermore, dyeings with the best wash fastness properties could be obtained if the agent as contemplated herein contains at least one organic silicon compound of formula (I) in which the radical a represents the number 3. In this case the radical b stands for the number 0.

In another preferred embodiment, an agent as contemplated herein contains (a) at least one organic silicon compound of formula (I),
where
R$_3$, R$_4$ independently of one another represent a methyl group or an ethyl group and
a stands for the number 3 and
b stands for the number 0.

Organic silicon compounds of the formula (I) which are particularly suitable for solving the problem as contemplated herein are

7

(3-Aminopropyl)triethoxysilan

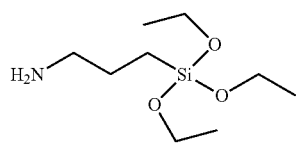

(3-Aminopropyl) trimethoxysilane

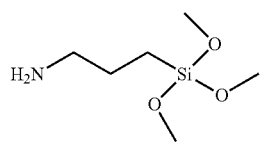

1-(3-Aminopropyl) silantriol

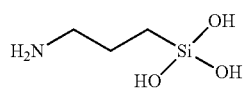

(2-Aminoethyl)triethoxysilan

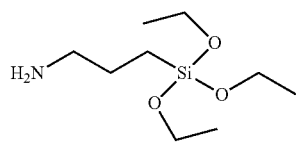

(2-Aminoethyl) trimethoxysilane

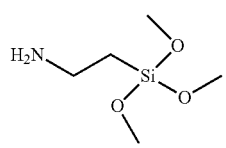

1-(2-Aminoethyl)silantriol

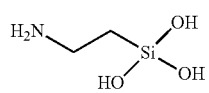

8

(3-Dimethylaminopropyl)triethoxysilan

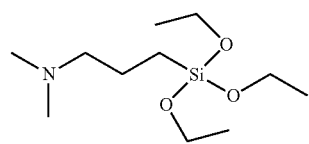 [SMILES: CCO[Si](CCCN(C)C)(OCC)OCC]

(3-Dimethylaminopropyl) trimethoxysilane

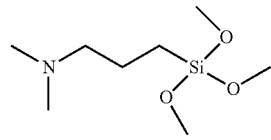

1-(3-Dimethylaminopropyl)silantriol

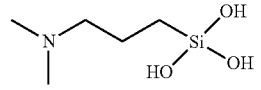

(2-Dimethylaminoethyl)triethoxysilan

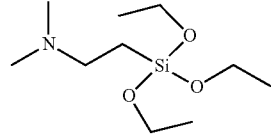

(2-Dimethylaminoethyl)trimethoxysilane and/or

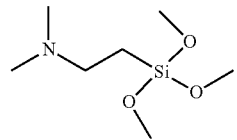

1-(2-Dimethylaminoethyl)silantriol

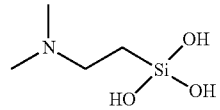

In another preferred embodiment, an agent as contemplated herein contains (a) at least one organic silicon compound of formula (I) selected from the group including
(3-Aminopropyl) triethoxysilane
(3-Aminopropyl) trimethoxysilane
1-(3-Aminopropyl) silantriol
(2-Aminoethyl) triethoxysilane
(2-Aminoethyl) trimethoxysilane
1-(2-Aminoethyl) silantriol
(3-Dimethylaminopropyl) triethoxysilan
(3-Dimethylaminopropyl) trimethoxysilane
1-(3-Dimethylaminopropyl) silantriol
(2-Dimethylaminoethyl) triethoxysilane
(2-Dimethylaminoethyl) trimethoxysilane and/or
1-(2-Dimethylaminoethyl) silantriol.

The organic silicon compound of formula (I) is commercially available. (3-aminopropyl)trimethoxysilane, for example, can be purchased from Sigma-Aldrich. Also (3-aminopropyl)triethoxysilane is commercially available from Sigma-Aldrich.

In a further version, the present disclosure contains at least one organic silicon compound of formula (II)

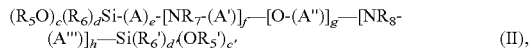
(II),

The organosilicon compounds of formula (II) as contemplated herein each carry the silicon-containing groups $(R_5O)_c(R_6)_d Si-$ and $-Si(R_6')_{d'}(OR_5')_c$ at both ends.

In the central part of the molecule of formula (II) there are the groups $-(A)_e-$ and $-[NR_7-(A')]_f-$ and $[O-(A'')]_g-$ and $-[NR_8-(A''')]_h-$. Here, each of the radicals e, f, g, and h can independently of one another stand for the number 0 or 1, with the proviso that at least one of the radicals e, f, g, and h is different from 0. In other words, an organic silicon compound of formula (II) as contemplated herein contains at least one grouping from the group including $-(A)-$ and $-[NR_7-(A')]-$ and $-[O-(A'')]-$ and $-[NR_8-(A''')]-$.

In the two terminal structural units $(R_5O)_c(R_6)_d Si-$ and $-Si(R_6')_{d'}(OR_5')_c$, the radicals R5, R5', R5" independently of one another represent a hydrogen atom or a $C_1-C_6$ alkyl group. The radicals R6, R6' and R6" independently represent a $C_1-C_6$ alkyl group.

Here a stands for an integer from 1 to 3, and d stands for the integer 3-c. If c stands for the number 3, then d is equal to 0. If c stands for the number 2, then d is equal to 1. If c stands for the number 1, then d is equal to 2.

Analogously c' stands for a whole number from 1 to 3, and d' stands for the whole number 3-c'. If c' stands for the number 3, then d' is 0. If c' stands for the number 2, then d' is 1. If c' stands for the number 1, then d' is 2.

Dyeings with the best wash fastness values could be obtained if the residues c and c' both stand for the number 3. In this case d and d' both stand for the number 0.

In another preferred embodiment, an agent as contemplated herein contains (a) at least one organic silicon compound of formula (II),

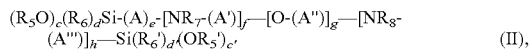
(II), where
R5 and R5' independently represent a methyl group or an ethyl group,
c and c' both stand for the number 3 and
d and d' both stand for the number 0.

If c and c' are both the number 3 and d and d' are both the number 0, the organic silicon compound of the present disclosure corresponds to formula (IIa)

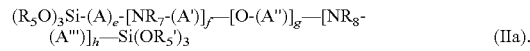
(IIa).

The radicals e, f, g, and h can independently stand for the number 0 or 1, whereby at least one radical from e, f, g, and h is different from zero. The abbreviations e, f, g and h thus define which of the groupings $-(A)e-$ and $-[NR_7-(A')]f-$ and $-[O-(A'')]g-$ and $-[NR_8-(A''')]h-$ are located in the middle part of the organic silicon compound of formula (II).

In this context, the presence of certain groupings has proved to be particularly beneficial in terms of increasing washability. Particularly good results were obtained when at least two of the residues e, f, g, and h stand for the number 1. It is especially preferred if e and f both stand for the number 1. Furthermore, g and h both stand for the number 0.

If e and f both stand for the number 1 and g and h both stand for the number 0, the organic silicon compound as contemplated herein corresponds to formula (IIb)

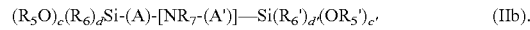
(IIb).

The radicals A, A', A", A''' and A"" independently represent a linear or branched divalent $C_1-C_{20}$ alkylene group. Preferably the radicals A, A', A", A''' and A"" independently of one another represent a linear, divalent $C_1-C_{20}$ alkylene group. Further preferably the radicals A, A', A", A''' and A"" independently represent a linear divalent $C_1-C_6$ alkylene group. In particular, the radicals A, A', A", A''' and A"" independently of one another represent a methylene group ($-CH_2-$), an ethylene group ($-CH_2-CH_2-$), a propylene group ($-CH_2-CH_2-CH_2-$) or a butylene group ($-CH_2-CH_2-CH_2-CH_2-$). In particular, the residues A, A', A", A''' and A"" stand for a propylene group ($-CH_2-CH_2-CH_2-$).

If the radical f represents the number 1, then the organic silicon compound of formula (II) as contemplated herein contains a structural grouping $-[NR_7-(A')]-$.

If the radical h represents the number 1, then the organic silicon compound of formula (II) as contemplated herein contains a structural grouping $-[NR_8-(A'''')]-$.

The radicals $R_7$ and $R_8$ independently represent a hydrogen atom, a $C_1-C_6$ alkyl group, a hydroxy-$C_1-C_6$ alkyl group, a $C_2-C_6$ alkenyl group, an amino-$C_1-C_6$ alkyl group or a group of the formula (III)

(III).

Very preferably the radicals R7 and R8 independently of one another represent a hydrogen atom, a methyl group, a 2-hydroxyethyl group, a 2-alkenyl group, a 2-aminoethyl group or a grouping of the formula (III).

If the radical f represents the number 1 and the radical h represents the number 0, the organic silicon compound as contemplated herein contains the grouping $[NR_7-(A')]$ but not the grouping $-[NR_8-(A''')]$. If the radical R7 now stands for a grouping of the formula (III), the pretreatment agents (A) contains an organic silicon compound with 3 reactive silane groups.

In another preferred embodiment, an agent as contemplated herein contains (a) at least one organic silicon compound of formula (II),

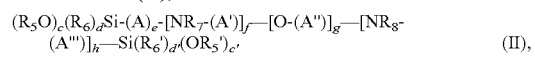
(II), where
e and f both stand for the number 1,
g and h both stand for the number 0,
A and A' independently represent a linear, divalent $C_1-C_6$ alkylene group and R7 represents a hydrogen atom, a methyl group, a 2-hydroxyethyl group, a 2-alkenyl group, a 2-aminoethyl group or a group of formula (III).

In a further preferred embodiment, an agent as contemplated herein contains (a) at least one organic silicon compound of formula (II), where e and f both stand for the number 1, g and h both stand for the number 0, A and A' independently of one another represent a methylene group (—CH$_2$—), an ethylene group (—CH$_2$—CH$_2$—) or a propylene group (—CH$_2$—CH$_2$—CH$_2$—), and R7 represents a hydrogen atom, a methyl group, a 2-hydroxyethyl group, a 2-alkenyl group, a 2-aminoethyl group or a group of formula (III).

Organic silicon compounds of the formula (II) which are particularly suitable for solving the problem as contemplated herein are 3-(trimethoxysilyl)-N-[3-(trimethoxysilyl)propyl]-1-propanamine

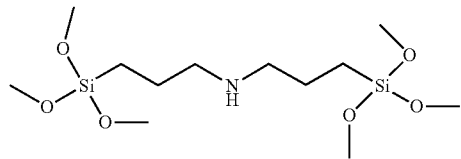

3-(Triethoxysilyl)-N-[3-(triethoxysilyl)propyl]-1-propanamine

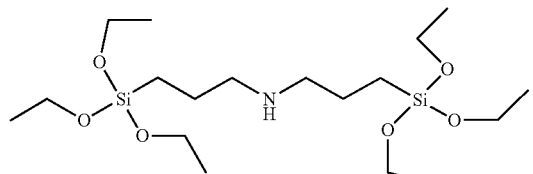

N-methyl-3-(trimethoxysilyl)-N-[3-(trimethoxysilyl)propyl]-1-propanamine

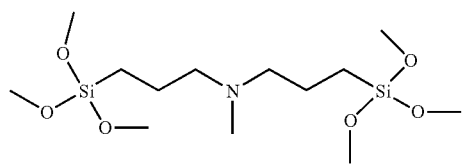

N-Methyl-3-(triethoxysilyl)-N-[3-(triethoxysilyl)propyl]-1-propanamine

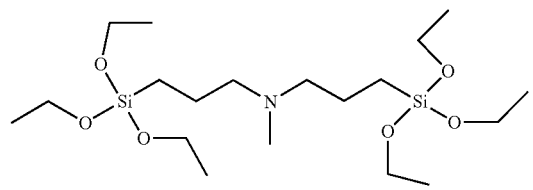 [SMILES: CCO[Si](CCCN(C)CCC[Si](OCC)(OCC)OCC)(OCC)OCC]

2-[Bis[3-(trimethoxysilyl)propyl]amino]-ethanol

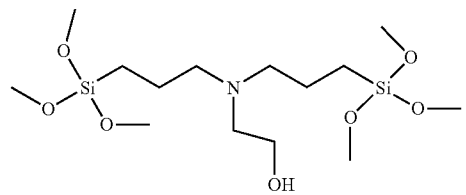

2-[Bis[3-(triethoxysilyl)propyl]amino]ethanol

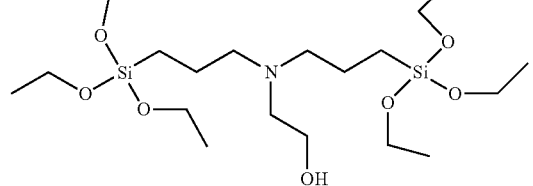

3-(Trimethoxysilyl)-N,N-bis[3-(trimethoxysilyl)propyl]-1-propanamine

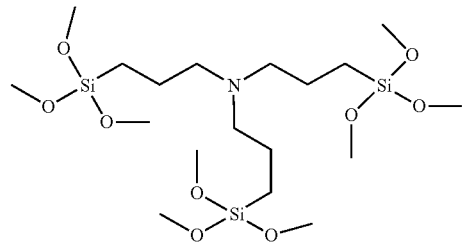

3-(Triethoxysilyl)-N,N-bis[3-(triethoxysilyl)propyl]-1-propanamine

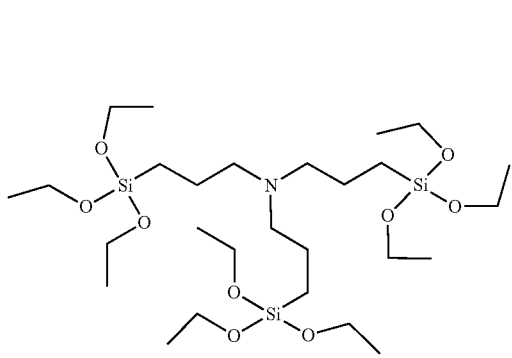 [SMILES: CCO[Si](CCCN(CCC[Si](OCC)(OCC)OCC)CCC[Si](OCC)(OCC)OCC)(OCC)OCC]

N1,N1-Bis[3-(trimethoxysilyl)propyl]-1,2-ethanediamine

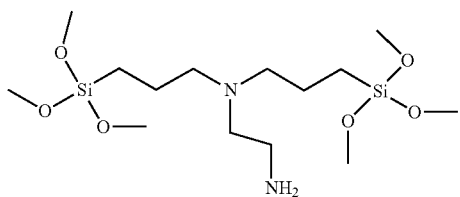

N1,N1-Bis[3-(triethoxysilyl)propyl]-1,2-ethanediamine

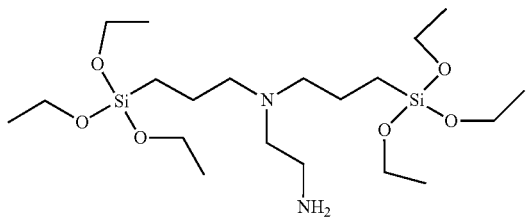 [SMILES: CCO[Si](CCCN(CCN)CCC[Si](OCC)(OCC)OCC)(OCC)OCC]

N,N-Bis[3-(trimethoxysilyl)propyl]-2-propen-1-amine

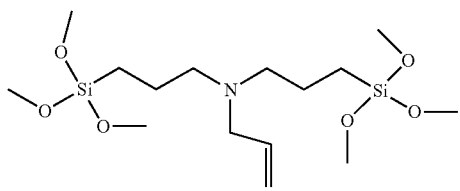

N,N-Bis[3-(triethoxysilyl)propyl]-2-propen-1-amine

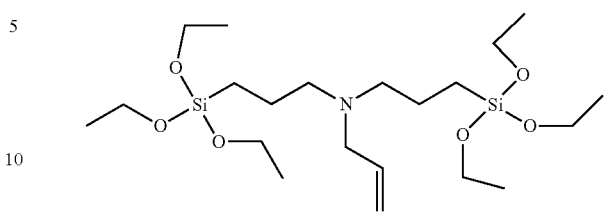

The organic silicon compounds of formula (II) are commercially available.
Bis(trimethoxysilylpropyl)amines with the CAS number 82985-35-1 can be purchased from Sigma-Aldrich.
Bis[3-(triethoxysilyl)propyl]amines with the CAS number 13497-18-2 can be purchased from Sigma-Aldrich, for example.
N-Methyl-3-(trimethoxysilyl)-N-[3-(trimethoxysilyl)propyl]-1-propanamine is alternatively referred to as Bis(3-trimethoxysilylpropyl)-N-methylamine and can be purchased commercially from Sigma-Aldrich or Fluorochem.
3-(Triethoxysilyl)-N,N-bis[3-(triethoxysilyl)propyl]-1-propanamine with the CAS number 18784-74-2 can be purchased for example from Fluorochem or Sigma-Aldrich.

In another preferred embodiment, an agent as contemplated herein contains (a) at least one organic silicon compound of formula (II) selected from the group including
3-(Trimethoxysilyl)-N-[3-(trimethoxysilyl)propyl]-1-propanamine
3-(Triethoxysilyl)-N-[3-(triethoxysilyl)propyl]-1-propanamine
N-Methyl-3-(trimethoxysilyl)-N-[3-(trimethoxysilyl)propyl]-1-propanamine
N-Methyl-3-(triethoxysilyl)-N-[3-(triethoxysilyl)propyl]-1-propanamine
2-[Bis[3-(trimethoxysilyl)propyl]amino]-ethanol
2-[Bis[3-(triethoxysilyl)propyl]amino]ethanol
3-(Trimethoxysilyl)-N,N-bis[3-(trimethoxysilyl)propyl]-1-Propanamine
3-(Triethoxysilyl)-N,N-bis[3-(triethoxysilyl)propyl]-1-Propanamine
N1,N1-Bis[3-(trimethoxysilyl)propyl]-1,2-Ethanediamine,
N1,N1-Bis[3-(triethoxysilyl)propyl]-1,2-Ethanediamine,
N,N-Bis[3-(trimethoxysilyl)propyl]-2-Propen-1-amine and/or
N,N-Bis[3-(triethoxysilyl)propyl]-2-Propen-1-amine.

The organic silicon compounds of formula (I) and (II) are reactive compounds. In this context, it has been found to be preferred if the composition of the present disclosure contains—based on its total weight—one or more organic silicon compounds (a) in a total amount of from about 0.1 to about 20.0% by weight, preferably from about 0.2 to about 15.0% by weight and particularly preferably from about 0.2 to about 2.0% by weight.

In this context, it has turned out to be particularly preferred if the agent of the present disclosure contains—based on its total weight—one or more organic silicon compounds (a) of the formula (I) and/or (II) in a total amount of from about 0.1 to about 20.0% by weight, preferably from about 0.2 to about 15.0% by weight and particularly preferably from about 0.2 to about 2.0% by weight.

It has been shown to be particularly suitable to use at least one organic silicon compound of formula (I) in the present disclosure.

In another preferred embodiment, an agent as contemplated herein contains (a) at least one organic silicon compound of formula (I).

Coloring Compounds from the Group of Pigments and/or Direct Dyes

As a second ingredient (b) essential to the present disclosure, the compositions as contemplated herein contain at least one coloring compound from the group of pigments and/or direct dyes.

Pigments within the meaning of the present disclosure are coloring compounds which have a solubility in water at about 25° C. of less than about 0.5 g/L, preferably less than about 0.1 g/L, even more preferably less than about 0.05 g/L. Water solubility can be determined, for example, by the method described below: about 0.5 g of the pigment are weighed in a beaker. A stir bar is added. Then one liter of distilled water is added. This mixture is heated to about 25° C. for one hour while stirring on a magnetic stirrer. If undissolved components of the pigment are still visible in the mixture after this period, the solubility of the pigment is below about 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below about 0.5 g/L.

Suitable color pigments can be of inorganic and/or organic origin.

In a preferred embodiment, an agent as contemplated herein contains (b) at least one coloring compound from the group of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. In particular, preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, an agent as contemplated herein contains (b) at least one colorant compound from the group of pigments selected from the group of colored metal oxides, metal hydroxides, metal oxide hydrates, silicates, metal sulfides, complex metal cyanides, metal sulfates, bronze pigments and/or from colored pigments based on mica or mica which are coated with at least one metal oxide and/or one metal oxychloride.

In a further preferred embodiment, an agent as contemplated herein contains (b) at least one colorant compound from the group of pigments selected from pigments based on mica, or mica which is combined with one or more metal oxides from the group of titanium dioxide (CI 77891), are coated with black iron oxide (CI 77499), yellow iron oxide (CI 77492), red and/or brown iron oxide (CI 77491, CI 77499), manganese violet (CI 77742), ultramarine (sodium aluminum sulfo-silicates, CI 77007, pigment blue 29), hydrated chromium oxide (CI 77289), chromium oxide (CI 77288) and/or iron blue (ferric ferrocyanides, CI 77510).

Examples of particularly suitable color pigments are commercially available under the trade names Rona®, Colorona®, Xirona®, Dichrona® and Timiron® from Merck®, Ariabel® and Unipure® from Sensient®, Prestige® from Eckart® Cosmetic Colors and Sunshine® from Sunstar®.

Particularly preferred color pigments with the trade name Colorona® are, for example:

Colorona® Copper, Merck®, MICA, CI 77491 (IRON OXIDES)

Colorona® Passion Orange, Merck®, Mica, CI 77491 (Iron Oxides), Alumina

Colorona® Patina Silver, Merck®, MICA, CI 77499 (IRON OXIDES), CI 77891 (TITANIUM DIOXIDE)

Colorona® RY, Merck®, CI 77891 (TITANIUM DIOXIDE), MICA, CI 75470 (CARMINE)

Colorona® Oriental Beige, Merck®, MICA, CI 77891 (TITANIUM DIOXIDE), CI 77491 (IRON OXIDES)

Colorona® Dark Blue, Merck®, MICA, TITANIUM DIOXIDE, FERRIC FERROCYANIDE

Colorona® Chameleon, Merck®, CI 77491 (IRON OXIDES), MICA

Colorona® Aborigine Amber, Merck®, CI 77499 (IRON OXIDES), CI 77891 (TITANIUM DIOXIDE)

Colorona® Blackstar Blue, Merck®, CI 77499 (IRON OXIDES), MICA

Colorona® Patagonian Purple, Merck®, MICA, CI 77491 (IRON OXIDES), CI 77891 (TITANIUM DIOXIDE), CI 77510 (FERRIC FERROCYANIDE)

Colorona® Red Brown, Merck®, MICA, CI 77491 (IRON OXIDES), CI 77891 (TITANIUM DIOXIDE)

Colorona® Russet, Merck®, CI 77491 (TITANIUM DIOXIDE), MICA, CI 77891 (IRON OXIDES)

Colorona® Imperial Red, Merck®, MICA, TITANIUM DIOXIDE (CI 77891), D&C RED NO. 30 (CI 73360)

Colorona® Majestic Green, Merck®, CI 77891 (TITANIUM DIOXIDE), MICA, CI 77288 (CHROMIUM OXIDE GREENS)

Colorona® Light Blue, Merck®, MICA, TITANIUM DIOXIDE (CI 77891), FERRIC FERROCYANIDE (CI 77510)

Colorona® Red Gold, Merck®, MICA, CI 77891 (TITANIUM DIOXIDE), CI 77491 (IRON OXIDES)

Colorona® Gold Plus MP 25, Merck®, MICA, TITANIUM DIOXIDE (CI 77891), IRON OXIDES (CI 77491)

Colorona® Carmine Red, Merck®, MICA, TITANIUM DIOXIDE, CARMINE

Colorona® Blackstar Green, Merck®, MICA, CI 77499 (IRON OXIDES)

Colorona® Bordeaux, Merck®, MICA, CI 77491 (IRON OXIDES)

Colorona® Bronze, Merck®, MICA, CI 77491 (IRON OXIDES)
Colorona® Bronze Fine, Merck®, MICA, CI 77491 (IRON OXIDES)
Colorona® Fine Gold MP 20, Merck®, MICA, CI 77891 (TITANIUM DIOXIDE), CI 77491 (IRON OXIDES)
Colorona® Sienna Fine, Merck®, CI 77491 (IRON OXIDES), MICA
Colorona® Sienna, Merck®, MICA, CI 77491 (IRON OXIDES)
Colorona® Precious Gold, Merck®, Mica, CI 77891 (Titanium dioxide), Silica, CI 77491 (Iron oxides), Tin oxide
Colorona® Sun Gold Sparkle MP 29, Merck®, MICA, TITANIUM DIOXIDE, IRON OXIDES, MICA, CI 77891, CI 77491 (EU)
Colorona® Mica Black, Merck®, CI 77499 (Iron oxides), Mica, CI 77891 (Titanium dioxide)
Colorona® Bright Gold, Merck®, Mica, CI 77891 (Titanium dioxide), CI 77491 (Iron oxides)
Colorona® Blackstar Gold, Merck®, MICA, CI 77499 (IRON OXIDES)

Other particularly preferred color pigments with the trade name Xirona® are for example:
Xirona® Golden Sky, Merck®, Silica, CI 77891 (Titanium Dioxide), Tin Oxide
Xirona® Caribbean Blue, Merck®, Mica, CI 77891 (Titanium Dioxide), Silica, Tin Oxide
Xirona® Kiwi Rose, Merck®, Silica, CI 77891 (Titanium Dioxide), Tin Oxide
Xirona® Magic Mauve, Merck®, Silica, CI 77891 (Titanium Dioxide), Tin Oxide.

In addition, particularly preferred color pigments with the trade name Unipure LC® are for example:
Unipure Red LC® 381 EM, Sensient® CI 77491 (Iron Oxides), Silica
Unipure Black LC® 989 EM, Sensient®, CI 77499 (Iron Oxides), Silica
Unipure Yellow LC® 182 EM, Sensient®, CI 77492 (Iron Oxides), Silica In a further embodiment, the compositions as contemplated herein may also contain (b) one or more coloring compounds from the group of organic pigments The organic pigments as contemplated herein are correspondingly insoluble, organic dyes or color lacquers, which may be selected, for example, from the group of nitroso, nitro-azo, xanthene, anthraquinone, isoindolinone, isoindoline, quinacridone, perinone, perylene, diketo-pyrrolopyorrole, indigo, thioindigo, dioxazine and/or triarylmethane compounds.

Examples of particularly suitable organic pigments are carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, an agent as contemplated herein contains (b) at least one colorant compound from the group of organic pigments selected from the group of carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles comprising a layer of absorbed dyes, the unit of particle and dye being insoluble under the above-mentioned conditions. The particles can, for example, be inorganic substrates, which can be aluminum, silica, calcium borosilicate, calcium aluminum borosilicate or even aluminum.

For example, alizarin color varnish can be used.

Due to their excellent resistance to light and temperature, the use of the pigments in the compositions as contemplated herein is particularly preferred. It is also preferred if the pigments used have a certain particle size. This particle size leads on the one hand to an even distribution of the pigments in the formed polymer film and on the other hand avoids a rough hair or skin feeling after application of the cosmetic product. As contemplated herein, it is therefore advantageous if the at least one pigment has an average particle size $D50$ of from about 1.0 to about 50 µm, preferably from about 5.0 to about 45 µm, preferably from about 10 to about 40 µm, especially from about 14 to about 30 µm. The mean particle size $D50$, for example, can be determined using dynamic light scattering (DLS).

The pigment or pigments (b) may be used in an amount of from about 0.001 to about 20% by weight, especially from about 0.05 to about 5% by weight, in each case based on the total weight of the agent.

As coloring compounds (b), the compositions as contemplated herein may also contain one or more direct dyes. Direct dyes are dyes that are applied directly to the hair and do not require an oxidative process to form the color. Direct dyes are usually nitro phenylene diamines, nitroaminophenols, azo dyes, anthraquinones, triarylmethane dyes or indophenols.

The direct dyes within the meaning of the present disclosure have a solubility in water (760 mmHg) at about 25° C. of more than about 0.5 g/L and are therefore not to be regarded as pigments.

Preferably, the direct dyes within the meaning of the present disclosure have a solubility in water (about 760 mmHg) at about 25° C. of more than about 1.0 g/L.

Direct dyes can be divided into anionic, cationic, and non-ionic direct dyes.

In a further preferred embodiment, an agent as contemplated herein contains as coloring compound (b) at least one anionic, cationic and/or non-ionic direct dye.

In a further preferred embodiment, an agent as contemplated herein contains (b) at least one anionic, cationic and/or non-ionic direct dye.

Suitable cationic direct dyes include Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51, and Basic Red 76.

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol.

In the course of the work leading to this present disclosure, it has been found that dyes with particularly high color intensity can be produced, with agents containing (b) at least one anionic direct dye.

In an explicitly particularly preferred embodiment, an agent as contemplated herein contains (b) at least one anionic direct dye.

Anionic direct dyes are also called acid dyes. Acid dyes are direct dyes that have at least one carboxylic acid group (—COOH) and/or one sulphonic acid group (—$SO_3H$). Depending on the pH value, the protonated forms (—COOH, —$SO_3H$) of the carboxylic acid or sulphonic acid groups are in equilibrium with their deprotonated forms (—COO⁻, —$SO_3$— present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Acid dyes can also be used in the form of their sodium salts and/or their potassium salts.

The acid dyes within the meaning of the present disclosure have a solubility in water (about 760 mmHg) at about 25° C. of more than about 0.5 g/L and are therefore not to be regarded as pigments. Preferably the acid dyes within the meaning of the present disclosure have a solubility in water (about 760 mmHg) at about 25° C. of more than about 1.0 g/L.

The alkaline earth salts (such as calcium salts and magnesium salts) or aluminum salts of acid dyes often have a lower solubility than the corresponding alkali salts. If the solubility of these salts is below about 0.5 g/L (about 25° C., about 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In the context of an embodiment, an agent for coloring keratinous material is thus preferred, which (b) contains at least one anionic direct dye selected from the group including nitrophenylenediamines, nitroaminophe-nols, azo dyes, anthraquinone dyes, triarylmethane dyes, xanthene dyes, rhodamine dyes, oxazine dyes and/or indophenol dyes, wherein the dyes from the aforementioned group each have at least one carboxylic acid group (—COOH), a sodium carboxylate group (—COONa), a potassium carboxylate group (—COOK), a sulphonic acid group (—$SO_3H$), a sodium sulphonate group (—$SO_3Na$) and/or a potassium sulphonate group (—$SO_3K$).

For example, one or more compounds from the following group can be selected as particularly well suited acid dyes: Acid Yellow 1 (D&C Yellow 7, Citronin A, Ext. D&C Yellow No. 7, Japan Yellow 403, CI 10316, COLIPA no B001), Acid Yellow 3 (COLIPA n°: C 54, D&C Yellow No 10, Quinoline Yellow, E104, Food Yellow 13), Acid Yellow 9 (CI 13015), Acid Yellow 17 (CI 18965), Acid Yellow 23 (COLIPA n °C. 29, Covacap Jaune W 1100 (LCW), Sicovit Tartrazine 85 E 102 (BASF®), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA n°C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I.14720), Acid Red 18 (E124, Red 18; CI 16255), Acid Red 27 (E 123, CI 16185, C-Rot 46, Echtrot D, FD&C Red Nr.2, Food Red 9, Naphthol Red S), Acid Red 33 (Red 33, Fuchsia Red, D&C Red 33, CI 17200), Acid Red 35 (CI C.I.18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI 27290), Acid Red 87 (Eosin, CI 45380), Acid Red 92 (COLIPA n°C53, CI 45410), Acid Red 95 (CI 45425, Erythtosines, Simacid Erythrosine Y), Acid Red 184 (CI 15685), Acid Red 195, Acid Violet 43 (Jarocol Violet 43, Ext. D&C Violet no 2, C.I. 60730, COLIPA n°C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido Blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant acid green BS, C.I. 44090, Acid Brilliant Green BS, E 142), Acid Black 1 (Black no 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. About 0.1 g of the anionic direct dye is placed in a beaker. A stir-bar is added. Then add about 100 ml of water. This mixture is heated to about 25° C. on a magnetic stirrer while stirring. It is stirred for about 60 minutes. The aqueous mixture is then visually assessed. If there are still undissolved residues, the amount of water is increased—for example in steps of 10 ml. Water is added until the amount of dye used is completely dissolved. If the dye-water mixture cannot be assessed visually due to the high intensity of the dye, the mixture is filtered.

If a proportion of undissolved dyes remains on the filter paper, the solubility test is repeated with a higher quantity of water. If about 0.1 g of the anionic direct dye dissolves in about 100 ml water at about 25° C., the solubility of the dye is about 1.0 g/L.

Acid Yellow 1 is called 8-hydroxy-5,7-dinitro-2-naphthalenesulfonic acid disodium salt and has a solubility in water of at least about 40 g/L about (25° C.).

Acid Yellow 3 is a mixture of the sodium salts of mono- and sisulfonic acids of 2-(2-quinolyl)-1H-indene-1,3(2H)-dione and has a water solubility of about 20 g/L (about 25° C.).

Acid Yellow 9 is the disodium salt of 8-hydroxy-5,7-dinitro-2-naphthalenesulfonic acid, its solubility in water is above about 40 g/L (about 25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at about 25° C.

Acid Orange 7 is the sodium salt of 4-[(2-hydroxy-1-naphthyl)azo]benzene sulphonate. Its water solubility is more than about 7 g/L (about 25° C.).

Acid Red 18 is the trisodium salt of 7-hydroxy-8-[(E)-(4-sulfonato-1-naphthyl)-diazenyl)]-1,3-naphthalene disulfate and has a very high-water solubility of more than about 20% by weight.

Acid Red 33 is the disodium salt of 5-amino-4-hydroxy-3-(phenylazo)-naphthalene-2,7-disulphonate, its solubility in water is about 2.5 g/L (about 25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than about 10 g/L (about 25° C.).

Acid Blue 9 is the disodium salt of 2-({4-[N-ethyl(3-sulfonatobenzyl)amino]phenyl}{4-[(N-ethyl(3-sulfonatobenzyl)imino]-2,5-cyclohexadien-1-ylidene}methyl)-benzenesulfonate and has a solubility in water of more than about 20% by weight (about 25° C.).

A particularly preferred composition of the present disclosure contains (b) at least one anionic direct dye from the group including Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct dyestuff(s), in the anionic direct dyestuff(s), can be used in different quantities in the compositions according to the desired color intensity. Particularly good results could be obtained if the agent as contemplated herein—based on its total weight—contains one or more direct dyes (b) in a total amount of from about 0.01 to about 10.0 wt. %, preferably from about 0.1 to about 8.0 wt. %, further preferably from about 0.2 to about 6.0 wt. % and very particularly preferably from about 0.5 to about 4.5 wt. %.

In a further preferred embodiment, an agent as contemplated herein contains—based on its total weight—one or more direct dyes (b) in a total amount of from about 0.01 to about 10.0% by weight, preferably from about 0.1 to about 8.0% by weight, more preferably from about 0.2 to about 6.0% by weight and very particularly preferably from about 0.5 to about 4.5% by weight.

In a further preferred version, an agent as contemplated herein contains—based on its total weight—one or more anionic direct-acting dyes (b) in a total amount of from about 0.01 to about 10.0% by weight, preferably from about 0.1 to about 8.0% by weight, more preferably from about 0.2 to about 6.0% by weight and very particularly preferably from about 0.5 to about 4.5% by weight.

Film-Forming, Hydrophilic Polymer

As the third ingredient essential to the present disclosure (c), the compositions as contemplated herein contain at least one film-forming, hydrophilic polymer.

Polymers are macromolecules with a molecular weight of at least about 1000 g/mol, preferably of at least about 2500 g/mol, particularly preferably of at least about 5000 g/mol, which include identical, repeating organic units. The polymers of the present disclosure may be synthetically produced polymers which are manufactured by polymerization of one type of monomer or by polymerization of different types of monomer which are structurally different from each other. If the polymer is produced by polymerizing a type of monomer, it is called a homo-polymer. If structurally different monomer types are used in polymerization, the resulting polymer is called a copolymer.

The maximum molecular weight of the polymer depends on the degree of polymerization (number of polymerized monomers) and the batch size and is determined by the polymerization method. For the purposes of the present disclosure, it is preferred that the maximum molecular weight of the film-forming hydrophobic polymer (c) is not more than about $10^7$ g/mol, preferably not more than about $10^6$ g/mol and particularly preferably not more than about $10^5$ g/mol.

A hydrophilic polymer is a polymer that has a solubility in water at about 25° C. (about 760 mmHg) of more than about 1% by weight, preferably more than about 2% by weight.

The water solubility of the film-forming, hydrophilic polymer can be determined in the following way, for example. About 1.0 g of the polymer is placed in a beaker, made up to about 100 g with water. A stir-bar is added, and the mixture is heated to about 25° C. on a magnetic stirrer while stirring. It is stirred for about 60 minutes. The aqueous mixture is then visually assessed. A completely dissolved polymer appears microscopically homogeneous. If the polymer-water mixture cannot be assessed visually due to a high turbidity of the mixture, the mixture is filtered. If no undissolved polymer remains on the filter paper, the solubility of the polymer is more than about 1% by weight.

As contemplated herein, a film-forming polymer is a polymer which can form a film on a substrate, for example on a keratinic material or a keratinic fiber. The formation of a film can be demonstrated, for example, by looking at the keratin material treated with the polymer under a microscope.

Nonionic, anionic, and cationic polymers can be used as film-forming, hydrophilic polymers.

Suitable film-forming hydrophilic polymers can be selected, for example, from the group of polyvinylpyrrolidone (co)polymers, polyvinyl alcohol (co)polymers, vinyl acetate (co)polymers, carboxyvinyl (co)polymers, acrylic acid (co)polymers, methacrylic acid (co)polymers, natural gums, polysaccharides and/or acrylamide (co)polymers.

Furthermore, it is particularly preferred to use polyvinylpyrrolidone (PVP) and/or a vinylpyrrolidone-containing copolymer as film-forming hydrophilic polymers.

In another particularly preferred embodiment, an agent as contemplated herein contains (c) at least one film-forming, hydrophilic polymer selected from the group including polyvinylpyrrolidone (PVP) and the copolymers of polyvinylpyrrolidone.

It is explicitly most preferred when the agent of the present disclosure contains polyvinylpyrrolidone (PVP) as a film-forming, hydrophilic polymer (c). Polyvinylpyrrolidone as a film-forming, hydrophilic polymer (c) could be dissolved very simply and easily in water and keep larger quantities of pigments stable in dispersion for a long time. Surprisingly, the wash fastness of dyeings obtained with formulations containing PVP was also particularly good.

Particularly well suited polyvinylpyrrolidones are, for example, available under the name Luviskol® K from BASF® SE, especially Luviskol® K 90 or Luviskol® K 85 from BASF® SE.

The polymer PVP K30, which is marketed by Ashland™ (ISP, POI Chemical), can also be used as another explicitly very well suited polyvinylpyrrolidone (PVP). PVP K 30 is a polyvinylpyrrolidone which is highly soluble in cold water and has the CAS number 9003-39-8. The molecular weight of PVP K 30 is about 40,000 g/mol.

Other particularly suitable polyvinylpyrrolidones are the substances known under the trade names LUVITEC K 17, LUVITEC K 30, LUVITEC K 60, LUVITEC K 80, LUVITEC K 85, LUVITEC K 90 and LUVITEC K 115 and available from BASF®.

The use of film-forming hydrophilic polymers (c) from the group of copolymers of polyvinylpyrrolidone has also led to particularly good and wash fast color results. The storage stability of formulations containing one or more copolymers of polyvinylpyrrolidone (c) was also particularly good.

Vinylpyrrolidone-vinyl ester copolymers, such as those marketed under the trademark Luviskol® (BASF®), are particularly suitable film-forming hydrophilic polymers. Luviskol® VA 64 and Luviskol® VA 73, both vinylpyrrolidone/vinyl acetate copolymers, are particularly preferred non-ionic polymers.

Of the vinylpyrrolidone-containing copolymers, a styrene/VP copolymer and/or a vinylpyrrolidone-vinyl acetate copolymer and/or a VP/DMAPA acrylates copolymer and/or a VP/vinyl caprolactam/DMAPA acrylates copolymer are particularly preferred in cosmetic compositions.

Vinylpyrrolidone-vinyl acetate copolymers are marketed under the name Luviskol® VA by BASF® SE. For example, a VP/Vinyl Caprolactam/DMAPA Acrylates copolymer is sold under the trade name Aquaflex® SF-40 by Ashland™ Inc. For example, a VP/DMAPA acrylates copolymer is marketed by Ashland™ under the name Styleze® CC-10 and is a highly preferred vinylpyrrolidone-containing copolymer.

Other suitable copolymers of polyvinylpyrrolidone (c) may also be those obtained by reacting N-vinylpyrrolidone with at least one further monomer from the group including V-vinylformamide, vinyl acetate, ethylene, propylene, acrylamide, vinyl caprolactam, vinyl caprolactone and/or vinyl alcohol.

In another particularly preferred embodiment, an agent as contemplated herein contains (c) at least one film-forming hydrophilic polymer selected from the group of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinyl caprolactam copolymers, vinylpyrrolidone/vinyl formamide copolymers and/or vinylpyrrolidone/vinyl alcohol copolymers.

Another suitable copolymer of vinylpyrrolidone is the polymer known under the INCI designation maltodextrin/VP copolymer.

Furthermore, intensively dyed keratin material, especially hair, with particularly good wash fastness could be obtained if a non-ionic, film-forming, hydrophilic polymer was used as the film-forming, hydrophilic polymer.

In a particularly preferred embodiment, an agent as contemplated herein contains (c) at least one non-ionic, film-forming, hydrophilic polymer.

As contemplated herein, a non-ionic polymer is understood to be a polymer which in a protic solvent—such as water—under standard conditions does not carry structural units with permanent cationic or anionic groups, which must be compensated by counterions while maintaining electron neutrality. Cationic groups include quaternized ammonium groups but not protonated amines. Anionic groups include carboxylic and sulphonic acid groups.

Preference is given to products containing, as a non-ionic, film-forming, hydrophilic polymer, at least one polymer selected from the group including Polyvinylpyrrolidone, Copolymers of N-vinylpyrrolidone and vinyl esters of carboxylic acids having 2 to 18 carbon atoms, in particular of N-vinylpyrrolidone and vinyl acetate, Copolymers of N-vinylpyrrolidone and N-vinyl imidazole and meth acrylamide, Copolymers of N-vinylpyrrolidone and N-vinyl imidazole and acrylamide, Copolymers of N-vinylpyrrolidone with N,N-di(C1 to C4)-alkylamino-(C2 to C4)-alkyl acrylamide, If copolymers of N-vinylpyrrolidone and vinyl acetate are used, it is again preferable if the molar ratio of the structural units contained in the monomer N-vinylpyrrolidone to the structural units of the polymer contained in the monomer vinyl acetate is in the range from about 20:80 to about 80:20, in particular from about 30:70 to about 60:40. Suitable copolymers of vinyl pyrrolidone and vinyl acetate are available, for example, under the trademarks Luviskol® VA 37, Luviskol® VA 55, Luviskol® VA 64 and Luviskol® VA 73 from BASF® SE.

Another particularly preferred polymer is selected from the INCI designation VP/Meth acrylamide/Vinyl Imidazole Copolymer, which is available under the trade name Luviset® Clear from BASF® SE.

Another particularly preferred non-ionic, film-forming, hydrophilic polymer is a copolymer of N-vinylpyrrolidone and N,N-dimethylaminiopropylmethacrylamide, which is sold under the INCI designation VP/DMAPA Acrylates Copolymer e.g. under the trade name Styleze® CC 10 by ISP.

A cationic polymer of interest is the copolymer of N-vinylpyrrolidone, N-vinyl caprolactam, N-(3-dimethylaminopropyl)meth acrylamide and 3-(methacryloylamino)propyl-lauryl-dimethylammonium chloride (INCI designation): Polyquaternium-69), which is marketed, for example, under the trade name AquaStyle® 300 (from about 28-32 wt. % active substance in ethanol-water mixture, molecular weight 350,000) by ISP.

Other suitable film-forming, hydrophilic polymers include

Vinylpyrrolidone-vinylimidazolium methochloride copolymers, as offered under the designations Luviquat® FC 370, FC 550 and the INCI designation Polyquaternium-16 as well as FC 905 and HM 552, Vinylpyrrolidone-vinyl caprolactam-acrylate terpolymers, as they are commercially available with acrylic acid esters and acrylic acid amides as a third monomer component, for example under the name Aquaflex® SF 40.

Polyquaternium-11 is the reaction product of diethyl sulphate with a copolymer of vinyl pyrrolidone and dimethylaminoethyl methacrylate. Suitable commercial products are available under the names Dehyquart® CC 11 and Luviquat® PQ 11 PN from BASF® SE or Gafquat® 440, Gafquat® 734, Gafquat® 755 or Gafquat® 755N from Ashland™ Inc.

Polyquaternium-46 is the reaction product of vinyl caprolactam and vinylpyrrolidone with methylvinylimidazolium methosulfate and is available for example under the name Luviquat® Hold from BASF® SE. Polyquaternium-46 is preferably used in an amount of 1 to 5% by weight—based on the total weight of the cosmetic composition. It is particularly preferred to use polyquaternium-46 in combination with a cationic guar compound. It is highly preferred that polyquaternium-46 is used in combination with a cationic guar compound and polyquaternium-11.

Suitable anionic film-forming, hydrophilic polymers can be, for example, acrylic acid polymers, which can be in non-crosslinked or crosslinked form. Such products are sold commercially under the trade names Carbopol® 980, 981, 954, 2984 and 5984 by Lubrizol® or under the names Synthalen® M and Synthalen® K by 3V Sigma® (The Sun Chemicals®, Inter Harz).

Examples of suitable film-forming, hydrophilic polymers from the group of natural gums are xanthan gum, gellan gum, and carob gum.

Examples of suitable film-forming hydrophilic polymers from the group of polysaccharides are hydroxyethyl cellulose, hydroxypropyl cellulose, ethyl cellulose and carboxymethyl cellulose.

Suitable film-forming, hydrophilic polymers from the group of acrylamides are, for example, polymers which are produced from monomers of (methyl)acrylamido-C1-C4-alkyl sulphonic acid or the salts thereof. Corresponding polymers may be selected from the polymers of polyacrylamidomethanesulfonic acid, polyacrylamidoethanesulfonic acid, polyacrylamidopropanesulfonic acid, poly2-acrylamido-2-methylpropanesulfonic acid, poly-2-methylacrylamido-2-methylpropanesulfonic acid and/or poly-2-methylacrylamido-n-butanesulfonic acid.

Preferred polymers of the poly(meth)arylamido-C1-C4-alkyl sulphonic acids are cross-linked and at least about 90% neutralized. These polymers may or may not be cross-linked.

Cross-linked and totally or partially neutralized polymers of the poly-2-acrylamido-2-methylpropane sulphonic acid type are known under the INCI designation "Ammonium Polyacrylamido-2-methyl propane sulphonates" or "Ammonium Polyacryldimethyltauramides".

Another preferred polymer of this type is the cross-linked poly-2-acrylamido-2-methyl-propanesulphonic acid polymer marketed by Clamant under the trade name Hostacerin® AMPS, which is partially neutralized with ammonia.

The film-forming hydrophilic polymer(s) (c) as contemplated herein are preferably used in certain quantity ranges in the compositions as contemplated herein. In this context, it has proved to be particularly preferred for the solution of the task as contemplated herein if the agent—based on its total weight—contains one or more polymers in a total amount of from about 0.1 to about 25.0% by weight, preferably from about 0.2 to about 20.0% by weight, further preferably from about 0.5 to about 15.0% by weight and very particularly preferably from about 1.0 to about 7.0% by weight.

In a further preferred embodiment, an agent as contemplated herein contains—based on its total weight—one or more film-forming hydrophobic hydrophilic polymers (c) in a total amount of from about 0.1 to about 25.0% by weight, preferably from about 0.2 to about 20.0% by weight, more preferably from about 0.5 to about 15.0% by weight and very particularly preferably from about 1.0 to about 7.0% by weight.

Water Content of the Agents

The composition as contemplated herein contains the essential ingredients (a), (b) and (c) in a cosmetic carrier, preferably in an aqueous or water-containing cosmetic carrier.

Without being bound to this theory, it is assumed that the organic silicon compound (a), which comprises one or more hydroxyl groups or hydrolysable groups per molecule, is hydrolyzed and/or oligomerized in the presence of the water. The resulting hydrolysis products or oligomers have a particularly high affinity to the surface of the Keratin material. In this way, the coloring compounds (b) together with the film-forming hydrophilic polymer (c) can form a stable and resistant film. In this context, it has proved to be particularly preferable if the agent—based on its total weight—has a water content of from about 15 to about 95% by weight, preferably from about 20 to about 95% by weight, more preferably from about 25 to about 95% by weight, still more preferably from about 30 to about 95% by weight and very preferably from about 45 to about 95% by weight.

In a further explicitly very particularly preferred form of execution, an agent as contemplated herein has—based on its total weight—a water content of from about 15 to about 95% by weight, preferably of from about 20 to about 95% by weight, more preferably of from about 25 to about 95% by weight, still more preferably of from about 30 to about 95% by weight and very particularly preferably of from about 45 to about 95% by weight.

Multi-Component Packaging Unit (Kit-of-Parts)

The agent of the first subject of the present disclosure described above is the coloring agent ready for use. Together with the organic silicon compound(s), it contains (a) a class of reactive compounds which can undergo hydrolysis and/or oligomerization in the presence of water as described above.

To increase storage stability, this agent is preferably provided to the user in the form of a multi-component packaging unit (kit-of-parts). Shortly before application on the keratinous material, the user can mix the different components of this packaging unit to produce the ready-to-use dye.

A second object of the present disclosure is a multi-component packaging unit (kit-of-parts) for dyeing keratinous material, in particular human hair, which separately includes a first container containing a cosmetic product (I) and
a second container containing a cosmetic product (II) and
a third container containing a cosmetic product (III),
where
the agent (I) contains at least one organic silicon compound (a) as already disclosed in detail in the description of the first subject matter of the present disclosure,
the agent (II) contains water and
the agent (III) contains at least one coloring compound
from the group of pigments and/or direct dyes (b) and at least one film-forming, hydrophilic polymer (c), as already disclosed in detail in the description of the first object of present disclosure.

In a particularly preferred version, the ready-to-use dye is produced by mixing agents (I), (II) and (III). In this version, all three agents (I), (II) and (III) are applied simultaneously to the keratinous material.

For example, the user can first mix or shake the agent (I) containing the organic silicon compound(s) (a) with the water-containing agent (II). The user can then add agent (III) containing the coloring compound(s) (b) and the film-forming hydrophilic polymer(s) (c) to the mixture of (I) and (II) and mix all three agents together.

In another particularly preferred version, it is also possible to apply agents (I), (II) and (III) successively on the keratinous material, so that the agents interact with each other only on the keratinous material.

For example, the user can first mix or shake the agent (I) containing the organic silicon compound(s) (a) with the water-containing agent (II). The user can now apply this mixture of (I) and (II) to the keratin materials—either directly after their production or after a short reaction time of from about 10 seconds to about 20 minutes. The user can then apply agent (III), which contains the coloring compounds (b) and the film-forming hydrophilic polymer (c), to the keratin material.

The agent (I) contains at least one organic silicon compound (a) as already disclosed in detail in the description of the first subject matter of the present disclosure. Preferably, agent (I) contains at least one organic silicon compound of formula (I) and/or (II), where the radicals may represent the, preferred and particularly preferred substitutes. As organic silicon compound (a) the substances already mentioned can also be used.

To provide a formulation that is as stable as possible during storage, the agent (I) itself is preferably packaged with low or no water.

A multi-component packaging unit (kit-of-parts) as contemplated herein includes the agent (I), where the agent (I)—based on the total weight of the agent (I)—contains a water content of less than about 10% by weight, preferably less than about 5% by weight, more preferably less than about 1% by weight, still more preferably less than about 0.1% by weight and very particularly preferably less than about 0.01% by weight.

Agent (II) contains water. A multi-component packaging unit (kit-of-parts) as contemplated herein includes the agent (II), where the agent (II)—based on the total weight of the agent (II)—has a water content of from about 15 to about 100% by weight, preferably of from about 35 to about 100% by weight, more preferably of from about 55 to about 100% by weight, still more preferably of from about 65 to about 100% by weight and very particularly preferably of from about 75 to about 100% by weight.

The agent (III) contains at least one coloring compound (b) and at least one film-forming hydrophilic polymer (c), as already disclosed in detail in the description of the first object of present disclosure.

In a particularly preferred form, the agent (III) contains the already mentioned, preferred and the particularly preferred pigments (b).

In a further preferred design, a multi-component packaging unit as contemplated herein includes the agent (III), where the agent (III) contains—based on the total weight of the agent (III)—one or more coloring compounds (b) in a total amount of from about 0.01 to about 10.0% by weight, preferably from about 0.1 to about 8.0% by weight, more preferably from about 0.2 to about 6.0% by weight and very particularly preferably from about 0.5 to about 4.5% by weight.

In a particularly preferred form, the agent (III) contains the preferred and the particularly preferred film-forming, hydrophilic polymers (c).

In a further preferred embodiment, a multi-component packaging unit as contemplated herein includes the agent (III), where the agent (III) contains—based on the total weight of agent (III)—one or more film-forming hydrophobic polymers (b) in a total amount of from about 0.1 to about 25.0% by weight, preferably from about 0.2 to about 20.0% by weight, more preferably from about 0.5 to about 15.0% by weight and very particularly preferably from about 1.0 to about 7.0% by weight.

The agents (I) and (II) or agents (I), (II) and (III) can be mixed in different quantities. For example, the first container may contain from about 5 g to about 200 g of the agent (I). The second container can contain from about 5 g to about 200 g of the agent (II). The third container can contain from about 5 b to about 200 g of the agent (III).

Other Ingredients

The subject matter described above, i.e. the ready-to-use composition of the first subject matter of the present disclosure, and also the kit-of-parts with agents (I), (II) and (III) of the kit of the second subject matter of the present disclosure, may also contain one or more optional ingredients.

The products may also contain one or more surfactants. The term surfactants refer to surface-active substances. A distinction is made between anionic surfactants including a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one —COO$^{(-)}$- or —SO$_3^{(-)}$ group in the molecule. Particularly suitable zwitterionic surfactants are the so-called betaines such as the N-alkyl-N,N-dimethylammoniumglycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, apart from a $C_8$-$C_{24}$ alkyl or acyl group, contain at least one free amino group and at least one —COOH— or —SO$_3$H group in the molecule and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkylbetaines, alkylamidobetaines, amino propionates, aminoglycinate, imidazoliniumbetaines and sulfobetaines.

Particularly preferred ampholytic surfactants are N-cocoalkylaminopropionate, cocoacylaminoethylaminopropionate and $C_{12}$-$C_{18}$ acylsarcosine.

The products may also additionally contain at least one non-ionic surfactant. Suitable non-ionic surfactants are alkyl polyglycosides as well as alkylene oxide addition products to fatty alcohols and fatty acids with 2 to 30 mol ethylene oxide per mol fatty alcohol or fatty acid. Preparations with good properties are also obtained if they contain as non-ionic surfactants fatty acid esters of ethoxylated glycerol reacted with at least 2 mol ethylene oxide. The non-ionic surfactants are used in a total quantity of from about 0.1 to about 45% by weight, preferably from about 1 to about 30% by weight and very preferably from about 1 to about 15% by weight—based on the total weight of the respective agent.

In addition, the products may also contain at least one cationic surfactant. Cationic surfactants are surfactants, i.e. surface-active compounds, each with one or more positive charges. Cationic surfactants contain only positive charges. Usually these surfactants are composed of a hydrophobic part and a hydrophilic head group, the hydrophobic part usually including a hydrocarbon backbone (e.g. including one or two linear or branched alkyl chains) and the positive charge(s) being located in the hydrophilic head group. Examples of cationic surfactants are quaternary ammonium compounds which, as hydrophobic radicals, may carry one or two alkyl chains with a chain length of 8 to 28 C atoms, quaternary phosphonium salts substituted with one or more alkyl chains with a chain length of 8 to 28 C atoms or tertiary sulfonium salts.

Furthermore, the cationic charge can also be part of a heterocyclic ring (e.g. an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of from about 0.1 to about 45 wt. %, preferably from about 1 to about 30 wt. % and most preferably from about 1 to about 15 wt. %—based on the total weight of the respective agent.

Furthermore, the compositions as contemplated herein may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule.

The anionic surfactants are used in a total quantity of from about 0.1 to about 45 wt. %, preferably from about 1 to about 30 wt. % and most preferably from about 1 to about 15 wt. %—based on the total weight of the respective agent.

They may also contain other active substances, auxiliaries and additives, such as solvents, fatty components such as $C_8$-$C_{30}$ fatty alcohols, $C_8$-$C_{30}$ fatty acid triglycerides, $C_8$-$C_{30}$ fatty acid monoglycerides, $C_8$-$C_{30}$ fatty acid diglycerides and/or hydrocarbons; structural agents such as glucose, maleic acid and lactic acid; hair conditioning compounds such as phospholipids, for example lecithin and cephalins; perfume oils, dimethylisosorbide and cyclodextrins; fiber structure-improving active substances, in particular mono-, di- and oligosaccharides such as glucose, galactose, fructose, fructose and lactose; dyes for coloring the composition; anti-dandruff active substances such as Piroctone Olamine, Zinc Omadine and Climbazol; amino acids and oligopeptides; protein hydrolysates on animal and/or vegetable basis, as well as in the form of their fatty acid condensation products or optionally anionic or cationically modified derivatives; vegetable oils; sunscreens and UV-blockers; active ingredients such as panthenol, pantothenic acid, pantolactone, allantoin, pyrrolidinonecarboxylic acids and their salts, and bisabolol; polyphenols, in particular hydroxycinnamic acids, 6,7-dihydroxycumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; and blowing agents such as propane-butane mixtures, $N_2O$, dimethyl ether, $CO_2$ and air.

The selection of these other substances will be made by the specialist according to the desired properties of the agents. Regarding other optional components and the quantities of these components used, explicit reference is made to the relevant manuals known to the specialist. The additional active ingredients and auxiliary substances are preferably used in the preparations as contemplated herein in quantities of from about 0.0001 to about 25 wt. % each, from about 0.0005 to about 15 wt. %, based on the total weight of the respective agent.

Process for Dyeing Keratin Materials

The agents described above—both the ready-to-use agent of the first subject-matter of the present disclosure and the agents of the multi-component packaging unit of the second subject-matter of the present disclosure—are used in processes for dyeing keratinous materials, in particular for dyeing human hair.

A third subject of the present disclosure is a process for dyeing keratinous material, in particular human hair, comprising the following steps in the order indicated:

(1) Application of a pre-treatment agent (V) to the keratinous material, the pre-treatment agent (V) containing, in an aqueous cosmetic carrier, at least one organic silicon compound (a) as already disclosed in detail in the description of the first subject-matter of the present disclosure, (2) Application of a coloring agent (F) to the keratinous material, the coloring agent containing at least one coloring compound from the group of pigments and/or direct dyes (b) and at least one film-forming hydrophilic polymer (c), as already disclosed in detail in the description of the first subject-matter of the present disclosure.

In other words, a third subject-matter of the present disclosure is a process for coloring keratinous material, in particular human hair, comprising the following steps in the order indicated:

(1) application of a pretreatment agent (V) to the keratinous material, the said pretreatment agent (V) comprising, in a water-containing cosmetic carrier, at least one organic silicon compound (a) chosen from silanes containing one, two or three silicon atoms, the said organic silicon compound also comprising one or more basic chemical functions and one or more hydroxyl or hydrolysable groups per molecule, and (2) Application of a coloring agent (F) to the keratinous material, the coloring agent comprising at least one pigment and/or the direct dyes (b) and at least one film-forming hydrophilic polymer (c), as already disclosed in detail in the description of the first article of the present disclosure.

In other words, a third subject-matter of the present disclosure is a process for coloring keratinous material, in particular human hair, comprising the following steps in the order indicated:

(1) application of a pretreatment agent (V) to the keratinous material, the said pretreatment agent (V) comprising, in a water-containing cosmetic carrier, at least one organic silicon compound (a) chosen from silanes containing one, two or three silicon atoms, the said organic silicon compound also comprising one or more basic chemical functions and one or more hydroxyl or hydrolysable groups per molecule, and (2) Application of a coloring agent (F) to the keratinous material, the coloring agent comprising at least one pigment (b) and at least one film-forming hydrophilic polymer (c), as already disclosed in detail in the description of the first subject-matter of the present disclosure.

In the process as contemplated herein, the keratin materials, in particular human hair, are first treated with a pretreatment agent (V). Subsequently, the actual colorant (F)—which in addition to the film-forming hydrophilic polymer contains the coloring compound(s)—is applied to the keratin materials.

Preferably, the pretreatment agent (V) itself does not contain any dyes or coloring compounds. The pre-treatment agent (V) is exemplified by its content of at least one reactive organic silicon compound (a). The reactive organic silicon compound(s) (a) functionalize the hair surface as soon as they encounter it. In this way a first, still uncolored film is formed. In the second step of the process, a coloring agent (F) is now applied to the hair. During the application of the colorant (F) on the keratin materials, a film is also formed on the—now already functionalized—hair surface, whereby the coloring compounds are now embedded in the film and thus deposited on the hair. The film produced "in situ" in this way, in which the coloring compound is embedded, is exemplified by outstanding wash fastness and a homogeneous color result.

The pre-treatment agent (V) represents the pre-treatment agent (V) ready for use. In particular, the pre-treatment agent (V) is a mixture of agents (I) and (II) of the multi-component packaging unit as contemplated herein. The pretreatment agent (V) thus contains at least one organic silicon compound (a) selected from silanes having one, two or three silicon atoms, the organic silicon compound further comprising one or more basic chemical functions and one or more hydroxyl groups or hydrolysable groups per molecule. Preferably the pretreatment agent (V) contains at least one organic silicon compound (a) of formula (I) and/or (II) described above, whereby the remainder may stand for the already mentioned, the preferred and the particularly preferred substitutes.

Furthermore, the pre-treatment agent (V) contains water, whereby the water comes from the agent (II) of the kit-of-parts as contemplated herein.

In a particularly preferred embodiment, a process includes where the pre-treatment agent (V) is prepared before application to the keratinous material by mixing a first agent (I) and a second agent (II), wherein the first agent (I) contains at least one organic silicon compound (a) as disclosed in detail in the description of the first and second subject matter of the present disclosure, and the agent (II) contains water.

It is preferred if the pre-treatment agent (V)—based on the total weight of the pre-treatment agent (V)—has a water content of from about 15 to about 95% by weight, preferably of from about 20 to about 95% by weight, more preferably of from about 25 to about 95% by weight, still more preferably of from about 30 to about 95% by weight and very particularly preferably of from about 45 to about 95% by weight.

In a further very particularly preferred form of execution, a process as contemplated herein includes where the pre-treatment agent (V)—based on the total weight of the pre-treatment agent—has a water content of from about 15 to about 95% by weight, preferably of from about 20 to about 95% by weight, more preferably of from about 25 to about 95% by weight, still more preferably of from about 30 to about 95% by weight and very particularly preferably of from about 45 to about 95% by weight.

Especially resistant dyeings could be obtained by using an alkaline pre-treatment agent (V). Preferably, the pretreatment agent (V) has a pH value of from about 7.0 to about 11.5, preferably from about 7.5 to about 11.0 and particularly preferably from about 8.0 to about 10.5.

In a further particularly preferred form of execution, a process as contemplated herein includes where the pretreatment agent (V) has a pH value of from about 7.0 to about 11.5, preferably of from about 7.5 to about 11.0 and particularly preferably of from about 8.0 to about 10.5.

To adjust this alkaline pH, the pre-treatment agent (V) preferably contains at least one alkalizing agent, which is added in an amount that ensures the adjustment of the optimal pH value for the hair treatment in question. The pH values for the purposes of the present disclosure are pH values measured at a temperature of about 22° C.

Depending on the choice of the desired pH value and depending on the presence of other components in the agent as contemplated herein, such as acidic or basic salts or buffer components, the amount of alkalizing agent added can vary, usually requiring amounts of from about 0.01 to about 15 wt. %.

As alkalizing agent, the pre-treatment agent (V) can contain for example ammonia, alkanolamines and/or basic amino acids.

The alkanolamines which can be used in the composition of the present disclosure are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, and 2-amino-2-methylpropan-1,3-diol.

The alkanolamines particularly preferred as contemplated herein are selected from 2-aminoethan-1-ol and/or 2-amino-2-methylpropan-1-ol. A particularly preferred embodiment of the agent as contemplated herein contains an alkanolamine selected from 2-aminoethan-1-ol and/or 2-amino-2-methylpropan-1-ol as alkalizing agent.

A particularly preferred embodiment of the agent as contemplated herein contains an alkanolamine selected from 2-aminoethan-1-ol and/or 2-amino-2-methylpropan-1-ol as alkalizing agent. Preferred amino acids are amino carboxylic acids, especially α-(alpha)-amino carboxylic acids and ω-amino carboxylic acids, whereby α-amino carboxylic acids are particularly preferred.

As contemplated herein, basic amino acids are those amino acids which have an isoelectric point pI of greater than about 7.0.

The basic α-amino carboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine, and histidine, especially preferably arginine and lysine. In another particularly preferred embodiment, an agent as contemplated herein includes where the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

In a further particularly preferred embodiment, a process as contemplated herein includes where the pretreatment agent (V) contains at least one alkalizing agent which is preferably selected from the group including ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Besides the alkalizing agents described above, experts are familiar with common acidifying agents for fine adjustment of the pH-value. As contemplated herein, preferred acidifiers are pleasure acids, such as citric acid, acetic acid, malic acid, or tartaric acid, as well as diluted mineral acids.

Following the application of the pre-treatment agent (V), the colorant (F) is applied to the keratin materials. The colorant (F) is the ready-to-use colorant (F).

The coloring agent (F) contains the direct dye(s) (b) and the hydrophobic film-forming polymer(s) (c) in a cosmetic carrier, preferably in a water-containing cosmetic carrier.

In a further very particularly preferred embodiment, a process as contemplated herein includes where the colorant (F)—based on the total weight of the colorant (F)—has a water content of from about 15 to about 95% by weight, preferably of from about 20 to about 95% by weight, more preferably of from about 25 to about 95% by weight, still more preferably of from about 30 to about 95% by weight and very particularly preferably of from about 45 to about 95% by weight.

To produce particularly wash-fast dyeings, it has also proved to be particularly preferred if the dye (F) is also alkaline and has a pH value of from about 7.0 to about 11.5, preferably from about 7.5 to about 11.0 and particularly preferably from about 8.0 to about 10.5.

In a further particularly preferred embodiment, a process as contemplated herein includes where the colorant (F) has a pH value of from about 7.0 to about 11.5, preferably of from about 7.5 to about 11.0 and particularly preferably of from about 8.0 to about 10.5.

To adjust this alkaline pH, the coloring agent (F) also contains preferably at least one alkalizing agent, added in an amount that ensures the adjustment of the optimal pH for the specific hair treatment. The pH values for the purposes of the present disclosure are pH values measured at a temperature of about 22° C.

The coloring agent (F) may contain at least one alkalizing agent from the group mentioned above. In particular, the coloring agent (F) contains at least one alkalizing agent preferably selected from the group including ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-Amino-2-methylpropan-1-ol, 1-amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate In a further particularly preferred embodiment, a process as contemplated herein includes where the colorant (F) contains at least one alkalizing agent which is preferably selected from the group including ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Procedural Steps

The technical application properties of the resulting dyeing can be further improved by selecting the optimum process conditions.

In the context of a further form of execution, a procedure comprising the following steps in the order indicated is particularly preferred (1) Application of the pre-treatment agent (V) on the keratinous material, (2) Allow the pre-treatment agent (V) to act for a period of from about 10 seconds to about 10 minutes, preferably from about 10 seconds to about 5 minutes, (3) if necessary, rinse out the pre-treatment agent (V), (4) Application of the coloring agent (F) on the keratinous material, (5) leave the dye (F) to act for a period of from about 30 seconds to about 30 minutes, preferably from about 30 seconds to about 10 minutes, and (6) application of a conditioner if necessary and (7) Rinse out the keratinous material.

In a first step (1), the pre-treatment agent (V) is applied to the keratin materials, especially human hair.

After application, the pre-treatment agent (V) can act on the keratin materials. In this context, application times from about 10 seconds to about 10 minutes, preferably from about 20 seconds to about 5 minutes and especially preferably from about 30 seconds to about 2 minutes on the hair have proven to be particularly beneficial. In a further preferred embodiment, a process as contemplated herein is exemplified by (2) Allow the pre-treatment agent (V) to act on the keratin materials for a period of from about 10 seconds to about 10 minutes, preferably from about 10 seconds to about 5 minutes and most preferably from about 30 seconds to about 2 minutes.

In a preferred embodiment of the process as contemplated herein, the pretreatment agent (V) can now be rinsed from the keratin materials before the coloring agent (F) is applied to the hair in the following step.

In a further embodiment, a process comprising the following steps in the order given is particularly preferred
(1) Application of the pre-treatment agent (V) on the keratinous material,
(2) Allow the pre-treatment agent (V) to act for a period of from about 10 seconds to about 10 minutes, preferably from about 10 seconds to about 5 minutes,
(3) Rinse out the pretreatment agent (V),
(4) Application of the coloring agent (F) on the keratinous material,
(5) leave the dye (F) to act for a period of from about 30 seconds to about 30 minutes, preferably from about 30 seconds to about 10 minutes, and
(6) application of a conditioner if necessary and
(7) Rinse out the keratinous material.

Dyeings with also good wash fastness properties were obtained when the dye (F) was applied to the keratin materials which were still exposed to the pretreatment agent (V).

In a further embodiment, a process comprising the following steps in the order given is particularly preferred
(1) Application of the pre-treatment agent (V) on the keratinous material,
(2) Allow the pre-treatment agent (V) to act for a period of from about 10 seconds to about 10 minutes, preferably from about 10 seconds to about 5 minutes,
(3) no rinsing of the pretreatment agent (V),
(4) Application of the coloring agent (F) on the keratinous material,
(5) leave the dye (F) to act for a period of from about 30 seconds to about 30 minutes, preferably from about 30 seconds to about 10 minutes, and
(6) application of a conditioner if necessary and
(7) Rinse out the keratinous material.

In step (4) the dye (F) is now applied to the keratin materials. After application, let the colorant (F) act on the hair.

The process as contemplated herein allows the production of dyeings with particularly good intensity and wash fastness, even with a short reaction time of the dye (F). Application times from about 10 seconds to about 10 minutes, preferably from about 20 seconds to about 5 minutes and most preferably from about 30 seconds to about 3 minutes on the hair have proven to be particularly beneficial.

In a further preferred embodiment, a process as contemplated herein is exemplified by
(5) Allow the dye (F) to act on the hair for a period of from about 10 seconds to about 10 minutes, preferably from about 20 seconds to about 5 minutes and most preferably from about 30 seconds to about 3 minutes.

In a further embodiment, a process comprising the following steps in the order given is particularly preferred
(1) Application of the pre-treatment agent (V) on the keratinous material,
(2) Allow the pre-treatment agent (V) to act for a period of from about 10 seconds to about 10 minutes, preferably from about 10 seconds to about 5 minutes,
(3) Rinse out the pretreatment agent (V),
(4) Application of the coloring agent (F) on the keratinous material,
(5) Allow the dye (F) to act on the hair for a period of from about 10 seconds to about 10 minutes, preferably from about 20 seconds to about 5 minutes and most preferably from about 30 seconds to about 3 minutes, and
(6) application of a conditioner if necessary and
(7) Rinse out the keratinous material.

After exposure to the colorant (F), a conditioner can now optionally be applied.

In a further embodiment, a process comprising the following steps in the order given is particularly preferred
(1) Application of the pre-treatment agent (V) on the keratinous material,
(2) Allow the pre-treatment agent (V) to act for a period of from about 10 seconds to about 10 minutes, preferably from about 10 seconds to about 5 minutes,
(3) Rinse out the pretreatment agent (V),
(4) Application of the coloring agent (F) on the keratinous material,
(5) Allow the dye (F) to act on the hair for a period of from about 10 seconds to about 10 minutes, preferably from about 20 seconds to about 5 minutes and most preferably from about 30 seconds to about 3 minutes, and
(6) Application of a conditioner and
(7) Rinse out the keratinous material.

Preferably, the conditioner contains at least one cationic and/or non-ionic surfactant.

Surprisingly, it turned out that using the conditioner—especially if it contains at least one cationic surfactant—may further improve the fastness of the dyeings obtained and further intensify the color result.

In a further preferred embodiment, a process as contemplated herein includes where the conditioner contains at least one cationic and/or non-ionic surfactant.

In another particularly preferred version, a process as contemplated herein includes where the conditioner contains at least one cationic surfactant.

To obtain a coloring that is as homogeneous and resistant as possible, it has been found to be particularly preferable if there is a maximum period of about 48 hours, preferably a maximum of about 24 hours, more preferably a maximum of about 12 hours and most preferably a maximum of about 6 hours between the application of the pre-treatment agent (V) and the application of the coloring agent (F).

In a further preferred embodiment, a process as contemplated herein includes where the pretreatment agent (V) and the coloring agent (F) are applied to the hair within a period of at most about 48 hours, preferably at most about 24 hours, more preferably at most about 12 hours and most preferably at most about 6 hours.

Regarding the other preferred embodiments of the multi-component packaging unit as contemplated herein and the processes as contemplated herein, what is said about the compositions as contemplated herein applies mutatis mutandis.

Examples

1. Formulations

The following formulations have been produced (unless otherwise indicated, all figures are in % by weight)

Pretreatment Agent (V)

| Agent (I) | (I) |
|---|---|
| (3-Aminopropyl)triethoxysilane | 0.3 g |

| Agent (II) | (II) |
|---|---|
| Sodium hydroxide | ad pH 10.0 |
| Water | ad 100 wt.-% |

By mixing 0.3 g of agent (I) and 100 g of agent (II), the pre-treatment agent (V) was prepared ready for use. This involved shaking agents (I) and (II) together for 3 minutes. Then the pre-treatment agent (V) was left to stand for about 5 minutes. The pH value of the ready-to-use pre-treatment agent (V) was about 10.

Coloring Agent (F)

| Agent (III) | V F1 | E F2 | V F3 | E F4 |
|---|---|---|---|---|
| Colorona ® Bronze (Merck ®, Mica, CI77491, Iron oxides, CI77019) | 2.0 | 2.0 | — | — |
| Unipure Red LC 3071 (Sensient ®, Aluminum hydroxide, CI 15850) | — | — | 3.0 | 3.0 |
| PVP K 30 (Ashland ™, ISP, Polyvinylpyrrolidone) | — | 9.0 | — | 9.0 |
| Dermacryl ® 79 (Akzo Nobel ®, Acrylates/Octylacrylamide Copolymer, CAS-No. 129702-02-9) | 9.0 | — | 9.0 | — |
| Ammonia (25% aqueous solution) | ad pH 10 | ad pH 10 | ad pH 10 | ad pH 10 |
| Water | ad 100 | ad 100 | ad 100 | ad 100 |

V = Comparison
E = according to the present disclosure

Conditioner (C)

| Cetearyl alcohol | 5.0 |
|---|---|
| Ceteareth-20 | 0.3 |
| Isopropyl myristate | 0.8 |
| Stearamidopropyldimethylamine | 0.4 |
| Quaternium-87 | 3.0 |
| Propylene glycol | 1.0 |
| Citric acid | 0.95 |
| Glyceryl stearate | 0.3 |
| Water | Ad 100 |

2. Application

One strand of hair at a time (Kerling, Euronature hair white) was dipped into the pre-treatment agent (V) and left there for 1 minute. Afterwards, excess pre-treatment agent was stripped from each strand of hair. Each strand of hair was washed out with water. Excess water was scraped off each strand of hair.

The strands of hair were then each dipped in one of the dyes (F) and left there for 1 minute.

The strands of hair were then each wetted with a small amount of the conditioner and then rinsed with water and dried. Afterwards the strands were visually evaluated.

| | Specimen | | | |
|---|---|---|---|---|
| | 1 | 2 | 3 | 4 |
| Pretreatment agent (V) | (V) | (V) | (V) | (V) |
| Coloring agent (F) | (F1) Colorona ® Bronze + Dermacryl ® 79 | (F2) Colorona ® Bronze + PVP K30 | (F3) Unipure Red LC ® 3071 + Dermacryl ® 79 | (F4) Unipure Red LC ® 3071 + PVP K 30 |
| Conditioner (C) | (C) | (C) | (C) | (C) |
| Coloring | bronze yellow | golden yellow | red | red |
| Color Intensity | +++ | +++ | +++ | +++ |
| Hair feeling | | | | |

3. Measurement of Storage Stability 100 g of each of the color creams F1 to F4 were filled into a glass container. Then the glass container was closed. Each container was then stored at room temperature for 4 weeks. After this storage period, the stability of the formulation was visually assessed.

| | V<br>F1 | E<br>F2 | V<br>F3 | E<br>F4 |
|---|---|---|---|---|
| Storage 4 weeks, room temperature | (F1)<br>Colorona ®<br>Bronze +<br>Dermacryl ® 79<br>Pigments deposit at the bottom of the vessel, separation visible | (F2)<br>Colorona ®<br>Bronze +<br>PVP K30<br>finely dispersed | (F3)<br>Unipure Red<br>LC ® 3071 +<br>Dermacryl ® 79<br>Pigments deposit at the bottom of the vessel, separation visible | (F4)<br>Unipure Red<br>LC ® 3071 +<br>PVP K 30<br>finely dispersed |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A composition for dyeing keratinous material, comprising in a cosmetic carrier
   (a) at least one organic silicon compound selected from silanes having one, two or three silicon atoms, said organic silicon compound further comprising one or more basic chemical functions and one or more hydroxyl groups or hydrolysable groups per molecule,
   (b) at least one colorant compound selected from the group of pigments, direct dyes, and combinations thereof, and
   (c) at least one film-forming hydrophilic polymer, wherein the film-forming hydrophilic polymer has a solubility in water at a temperature 25 degrees Celsius and a pressure of 760 millimeters of mercury of more than 1% by weight.

2. The composition according to claim 1, wherein the composition comprises (a) at least one organic silicon compound of formula (I) and/or (II), $$R_1R_2N\text{-}L\text{-}Si(OR_3)_a(R_4)_b \quad (I),$$

where
   $R_1$, and $R_2$ independently represent a hydrogen atom or a $C_1$-$C_6$ alkyl group,
   L is a linear or branched divalent $C_1$-$C_{20}$ alkylene group,
   R3 represents a hydrogen atom or a $C_1$-$C_6$ alkyl group,
   R4 represents a $C_1$-$C_6$ alkyl group,
   a, stands for an integer from 1 to 3, and
   b stands for the integer 3-a,

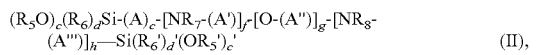

where
   R5, R5', and R5" independently represent a hydrogen atom or a $C_1$-$C_6$ alkyl group,
   R6, R6' and R6" independently represent a $C_1$-$C_6$ alkyl group,
   A, A', and A", independently of one another represent a linear or branched divalent $C_1$-$C_{20}$alkylene group,
   R7 and R8 independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group, or a group of formula (III)

where
   c, stands for an integer from 1 to 3,
   d stands for the integer 3-c,
   c' stands for an integer from 1 to 3,
   d' stands for the integer 3-c',
   c" stands for an integer from 1 to 3,
   d" stands for the integer 3-c",
   e stands for 0 or 1,
   f stands for 0 or 1,
   g stands for 0 or 1,
   h stands for 0 or 1,
   provided that at least one of e, f, g, and h is different from 0.

3. The composition according to claim 1, wherein the composition comprises (a) at least one organic silicon compound of the formula (I),

where
   $R_1$, $R_2$ both represent a hydrogen atom, and
   L represents a linear, divalent $C_1$-$C_6$ alkylene group.

4. The composition according to claim 2, wherein the composition comprises (a) at least one organic silicon compound of the formula (I),
where
   $R_3$, $R_4$ independently of one another represent a methyl group or an ethyl group and
   a stands for the number 3 and
   b stands for the number 0.

5. The composition according to claim 2 wherein the composition comprises (a) at least one organic silicon compound of the formula (I) which is selected from the group of
   (3-Aminopropyl) triethoxysilane
   (3-Aminopropyl)trimethoxysilane
   1-(3-Aminopropyl) silantriol
   (2-Aminoethyl) triethoxysilane
   (2-Aminoethyl) trimethoxysilane
   1-(2-Aminoethyl)silantriol
   (3-Dimethylaminopropyl) triethoxysilane
   (3-Dimethylaminopropyl) trimethoxysilane
   1-(3-Dimethylaminopropyl) silantriol (2-Dimethylaminoethyl)triethoxysilane,
(2-Dimethylaminoethyl) trimethoxysilane,
1-(2-Dimethylaminoethyl)silantriol, and combinations thereof.

6. The composition according to claim 2, wherein the composition comprises (a) at least one organic silicon compound of formula (II),
where
R5 and R5' independently represent a methyl group or an ethyl group,
c and c' both stand for the number 3 and
d and d' both stand for the number 0.

7. The composition according to claim 2, wherein the composition comprises (a) at least one organic silicon compound of formula (II),

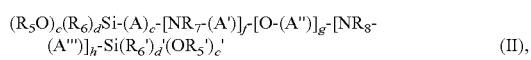

(II), where
e and f both stand for the number 1,
g and h both stand for the number 0,
A and A' independently represent a linear, divalent $C_1$-$C_6$ alkylene group, and
R7 represents a hydrogen atom, a methyl group, a 2-hydroxyethyl group, a 2-alkenyl group, a 2-aminoethyl group or a group of formula (III).

8. The composition according to claim 2, wherein the composition comprises (a) at least one organic silicon compound of the formula (II) which is selected from the group of
3-(trimethoxysilyl)-N-[3-(trimethoxysilyl)propyl]-1-propanamine,
3-(Triethoxysilyl)-N-[3-(triethoxysilyl)propyl]-1-propanamine,
N-methyl-3-(trimethoxysilyl)-N-[3-(trimethoxysilyl)propyl]-1-propanamine,
N-Methyl-3-(triethoxysilyl)-N-[3-(triethoxysilyl)propyl]-1-propanamine,
2-[Bis[3-(trimethoxysilyl)propyl]amino]-ethanol,
2-[bis[3-(triethoxysilyl)propyl]amino]ethanol,
3-(Trimethoxysilyl)-N,N-bis[3-(trimethoxysilyl)propyl]-1-propanamine,
3-(Triethoxysilyl)-N,N-bis[3-(triethoxysilyl)propyl]-1-propanamine,
N1,N1-bis[3-(trimethoxysilyl)propyl]-1,2-ethanediamine,
N1,N1-bis[3-(triethoxysilyl)propyl]-1,2-ethanediamine,
N,N-bis[3-(trimethoxysilyl)propyl]-2-propen-1-amine,
N,N-bis[3-(triethoxysilyl)propyl]-2-propen-1-amine, and combinations thereof.

9. The composition according to claim 1, wherein the film-forming hydrophilic polymer has a solubility in water at the temperature 25 degrees Celsius and the pressure of 760 millimeters of mercury of more than 2% by weight.

10. The composition according to claim 9, wherein the film-forming hydrophilic polymer comprises polyvinylpyrrolidone (PVP).

11. The composition according to claim 10, wherein the polyvinylpyrrolidone (PVP) has a molecular weight of about 40,000 g/mol.

12. A multicomponent packaging unit (kit-of-parts) for dyeing keratinous material comprising:
a first container containing a cosmetic product (I),
a second container containing a cosmetic product (II), and
a third container containing a cosmetic product (III),
where
the cosmetic product (I) comprises at least one organic silicon compound (a) selected from silanes having one, two or three silicon atoms, said organic silicon compound further comprising one or more basic chemical functions and one or more hydroxyl groups or hydrolysable groups per molecule,
the cosmetic product (II) comprises water, and
the cosmetic product (III) comprises at least one colorant compound (b) selected from the group of pigments, direct dyes, and combinations thereof, and at least one film-forming hydrophilic polymer (c), wherein the at least one film-forming hydrophilic polymer has a solubility of more than 1% by weight in water at a temperature of 25 degrees Celsius and a pressure of 760 millimeters of mercury.

13. The multicomponent packaging unit (kit-of-parts) according to claim 12, wherein the at least one film-forming hydrophilic polymer (c) comprises polyvinylpyrrolidone (PVP) with a solubility of more than 2% by weight in water at the temperature of 25 degrees Celsius and the pressure of 760 millimeters of mercury.

14. The multicomponent packaging unit (kit-of-parts) according to claim 13, wherein the cosmetic product (III) comprises the polyvinylpyrrolidone (PVP) in an amount of 9% by weight, based on a total weigh of the cosmetic product (III).

15. The multicomponent packaging unit (kit-of-parts) according to claim 14, wherein the polyvinylpyrrolidone (PVP) has a molecular weight of about 40,000 g/mol.

16. The agent according to claim 1, wherein the at least one film-forming hydrophilic polymer (c) is selected from the group of polyvinylpyrrolidone (PVP), vinylpyrrolidone/vinyl acetate copolymers, vinylpyrrolidone/styrene copolymers, Vinylpyrrolidone/ethylene copolymers, vinylpyrrolidone/propylene copolymers, vinylpyrrolidone/vinyl caprolactam copolymers, vinylpyrrolidone/vinyl formamide copolymers, vinylpyrrolidone/vinyl alcohol copolymers, and combinations thereof.

17. A method for dyeing keratinous material comprising the following steps in the order indicated:
(1) applying a pretreatment agent (V) to the keratinous material, the pretreatment agent (V) comprising, in a water-containing cosmetic carrier, at least one organic silicon compound (a) selected from silanes having one, two or three silicon atoms, said organic silicon compound further comprising one or more basic chemical functions and one or more hydroxyl groups or hydrolysable groups per molecule, and
(2) applying a coloring agent (F) to the keratinous material, the coloring agent comprising at least one colorant compound (b) selected from the group of pigments, direct dyes, and combinations thereof, and at least one film-forming hydrophilic polymer (c), wherein the at least one film-forming hydrophilic polymer has a solubility of more than 1% by weight in water at a temperature of 25 degrees Celsius and a pressure of 760 millimeters of mercury.

18. The method according to claim 17, further comprising: mixing a first agent (I) and a second agent (II) to produce the pre-treatment agent (V) before application on the keratinous material, wherein
the first agent (I) comprises the least one organic silicon compound (a),
the second agent (II) comprises water,
the at least one film-forming hydrophilic polymer has a solubility of more than 2% by weight in water at a temperature of 25 degrees Celsius and a pressure of 760 millimeters of mercury, the at least one film-forming hydrophilic polymer comprises polyvinylpyrrolidone (PVP), and the coloring agent (F) comprises the polyvinylpyrrolidone (PVP) in an amount of 9 weight percent, based on a total weight of the coloring agent (F).

19. A method according to claim 17, comprising the following steps in the order indicated
(1) applying the pre-treatment agent (V) onto the keratinous material,
(2) allowing the pre-treatment agent (V) to act for a period of from about 10 seconds to about 10 minutes,
(3) optionally rinsing out the pre-treatment agent (V),
(4) applying the coloring agent (F) onto the keratinous material,
(5) allowing the coloring agent (F) to react for a period of from about 30 seconds to about 30 minutes and
(6) optionally applying a conditioner, and
(7) rinsing the keratinous material.

20. The method according to claim 19, wherein the conditioner comprises at least one cationic and/or non-ionic surfactant.

* * * * *